United States Patent
Parvin et al.

(10) Patent No.: US 10,626,469 B2
(45) Date of Patent: Apr. 21, 2020

(54) RAPID IDENTIFICATION OF MICROORGANISMS

(71) Applicant: Board of Regents of the Nevada System of Higher Education, on behalf of the University of Nevada, Reno, Reno, NV (US)

(72) Inventors: Bahram Parvin, Reno, NV (US); Qingsu Cheng, Reno, NV (US)

(73) Assignee: Board of Regents of the Nevada System of Higher Education, on behalf of the University of Nevada, Reno, Reno, NV (US)

( * ) Notice: Subject to any disclaimer, the term of this patent is extended or adjusted under 35 U.S.C. 154(b) by 39 days.

(21) Appl. No.: 15/757,196

(22) PCT Filed: Sep. 2, 2016

(86) PCT No.: PCT/US2016/050122
§ 371 (c)(1),
(2) Date: Mar. 2, 2018

(87) PCT Pub. No.: WO2017/040939
PCT Pub. Date: Mar. 9, 2017

(65) Prior Publication Data
US 2018/0291432 A1    Oct. 11, 2018

Related U.S. Application Data

(60) Provisional application No. 62/214,687, filed on Sep. 4, 2015, provisional application No. 62/249,098, filed on Oct. 30, 2015.

(51) Int. Cl.
| | | |
|---|---|---|
| *C12Q 1/68* | (2018.01) | |
| *C12Q 1/689* | (2018.01) | |
| *A61K 31/713* | (2006.01) | |
| *C12Q 1/6841* | (2018.01) | |

(52) U.S. Cl.
CPC ............ *C12Q 1/689* (2013.01); *A61K 31/713* (2013.01); *C12Q 1/6841* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2010/0129808 A1 | 5/2010 | Mirkin et al. |
| 2012/0034162 A1 | 2/2012 | Barron et al. |
| 2012/0040349 A1 | 2/2012 | Von Lode et al. |
| 2015/0064265 A1 | 3/2015 | Fahmy et al. |

FOREIGN PATENT DOCUMENTS

WO    2011142838 A2    11/2011

OTHER PUBLICATIONS

Stewart et al, ACS Nano 7 (10), 9489 (Oct. 15, 2013).*
International Search Report and Written Opinion dated Nov. 15, 2016 from International Patent Application No. PCT/2016/050122.
Abdalhai, et al., Electrochemical Genosensor to Detect Pathogenic Bacteria (*Escherichia coli* O157:H7) as Applied in Real Food Samples (Fresh Beef) to Improve Food Safety and Quality Control., J Agric Food Chem. May 27, 2015;63(20):5017-25. doi: 10.1021/acs.jafc.5b00675. Epub May 19, 2015. (Abstract).
An, et al., DNA exposure to buckminsterfullerene (C60): toward DNA stability, reactivity, and replication., Environ Sci Technol. Aug. 1, 2011;45(15):6608-16. doi: 10.1021/es2012319. Epub Jul. 13, 2011. (Abstract).
Matos Pires, et al., Microfluidic biosensor array with integrated poly(2,7-carbazole)fullerene-based photodiodes for rapid multiplexed detection of pathogens., Sensors (Basel). Nov. 25, 2013;13(12):15898-911. doi: 103390/s131215898.

* cited by examiner

*Primary Examiner* — James Martinell
(74) *Attorney, Agent, or Firm* — Saul Ewing Arnstein & Lehr LLP; Kathryn Doyle

(57) ABSTRACT

Methods of labeling, identifying and differentiating microorganisms using functionalized Buckyballs are provided herein. The invention further provides methods for imaging or inhibiting gene expression using functionalized Buckyballs of the invention. The invention also provides a system for labeling, identifying and differentiating microorganisms.

50 Claims, 28 Drawing Sheets

$C_{60}$ Pyrrolidine tris-acid

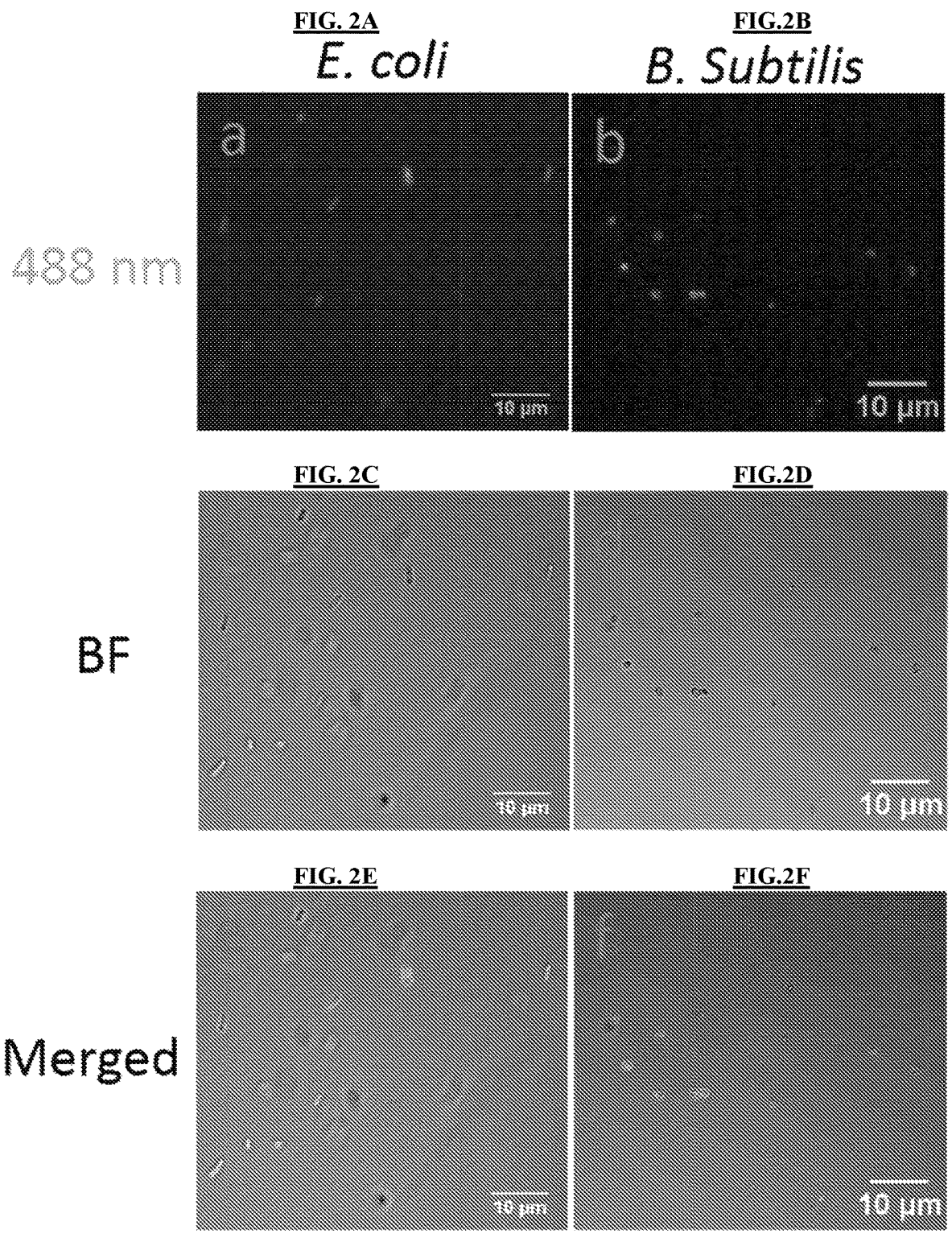

$^{14}C60$-pyrrolidine
tris acid+*E. coli*+Wash $^{14}C60$-pyrrolidine
tris acid+*B. subtilis*+Wash $^{125}I$-C60-pyrrolidine
tris acid+*E. coli*+Wash $^{125}I$-C60-pyrrolidine
tris acid+*B. subtilis*+Wash

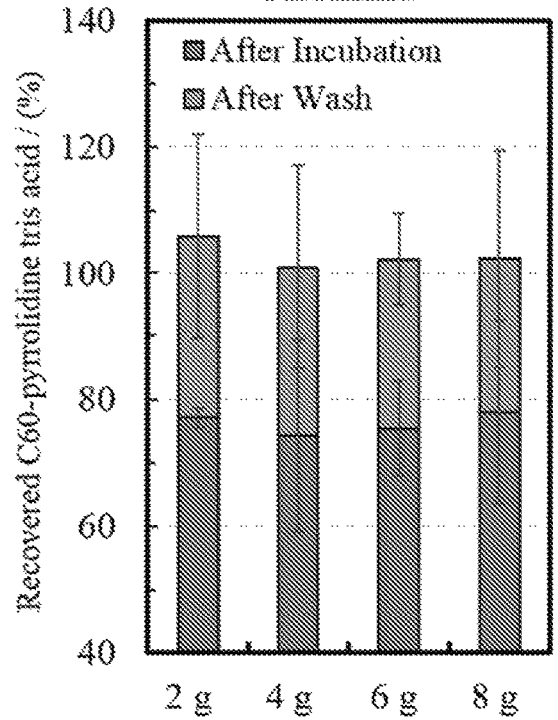
FIG. 5A Alumina
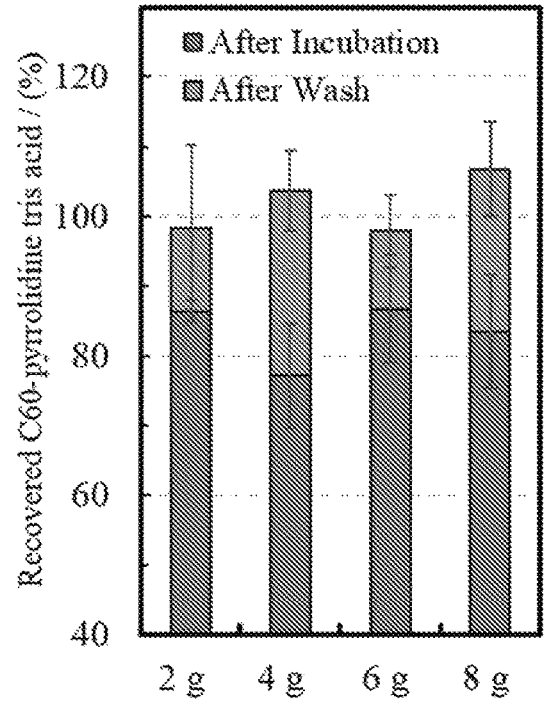
FIG. 5B VWR Sand
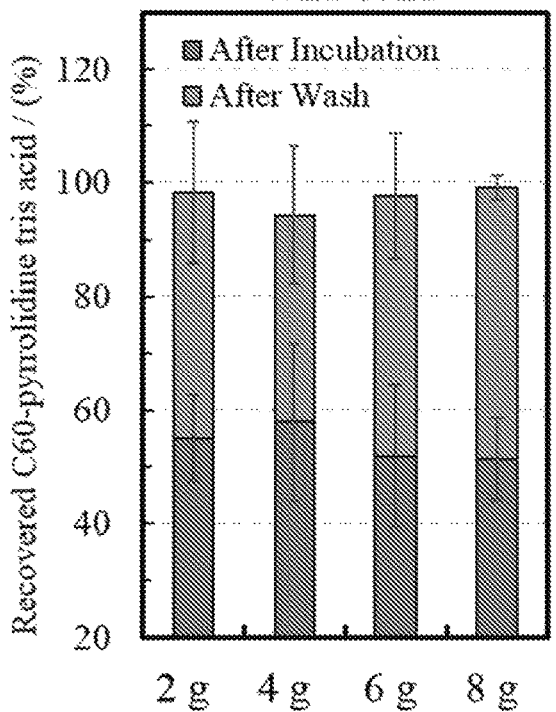
FIG. 5C Wild Sand
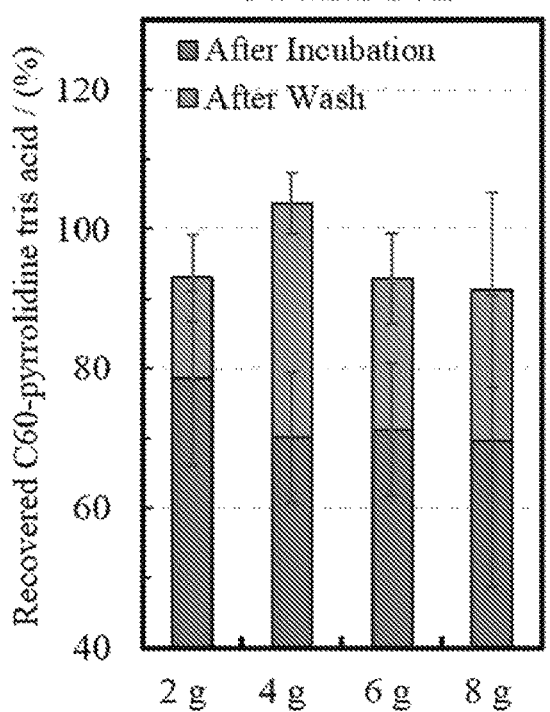
FIG. 5D Natural Soil

Alumina

Glass Beads

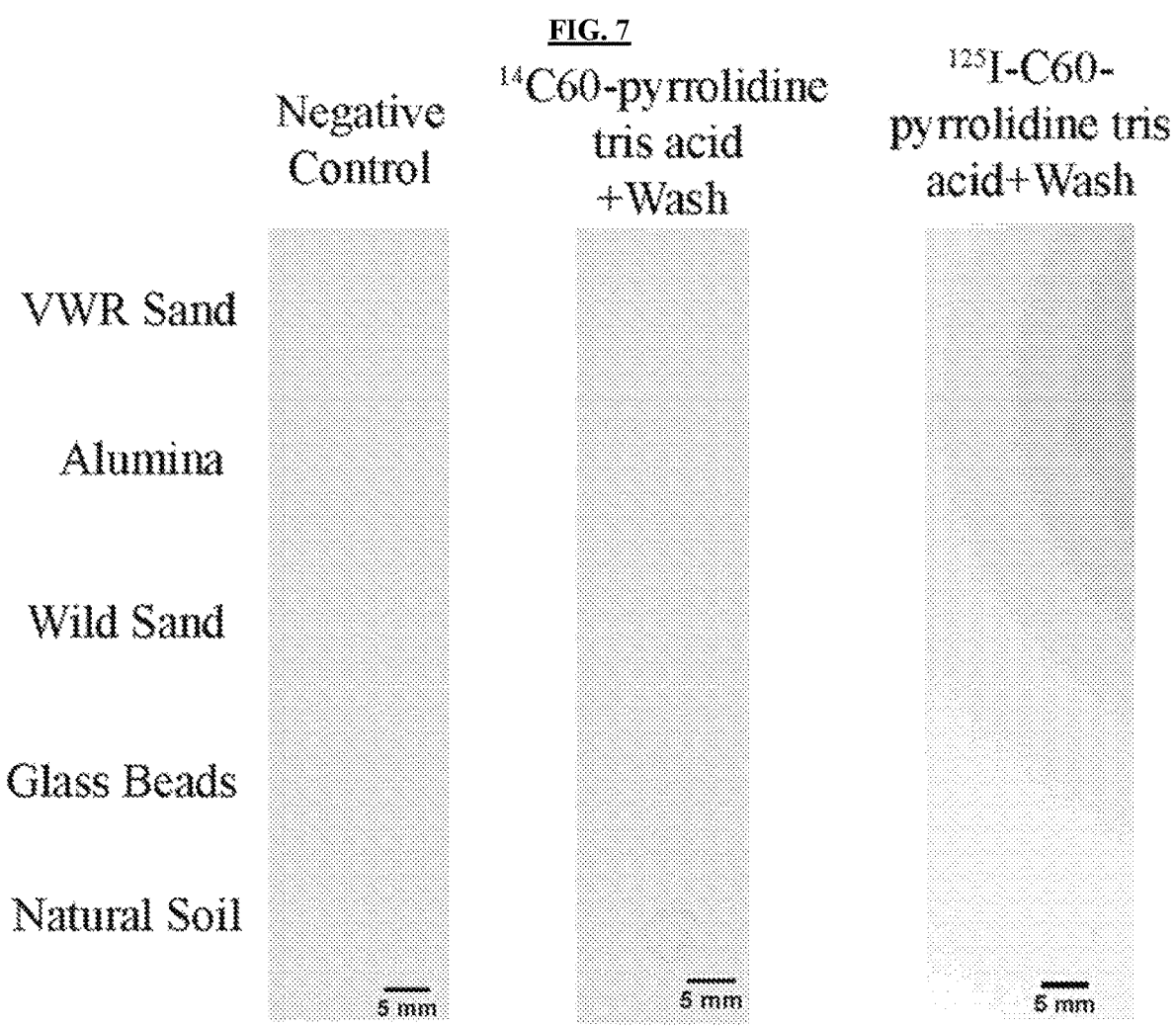

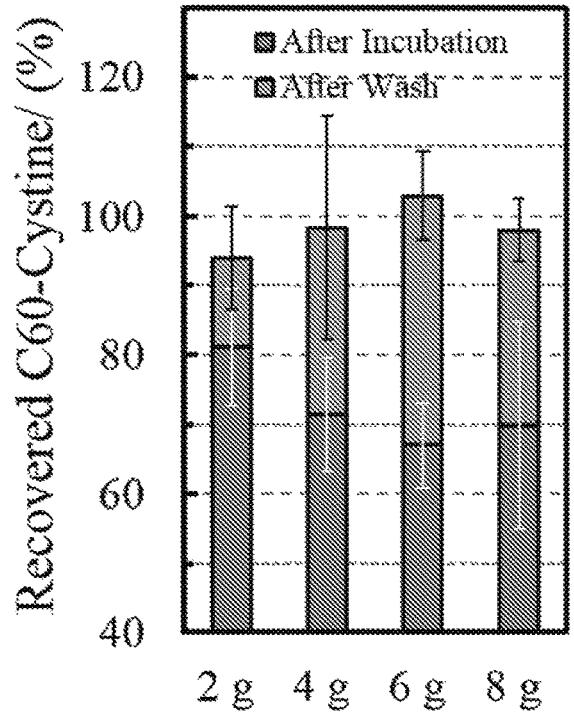
FIG. 10A Alumina
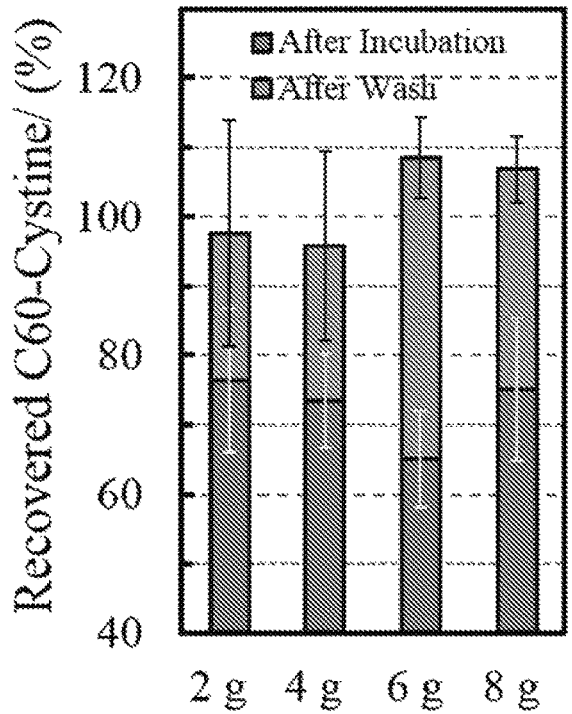
FIG. 10B VWR Sand
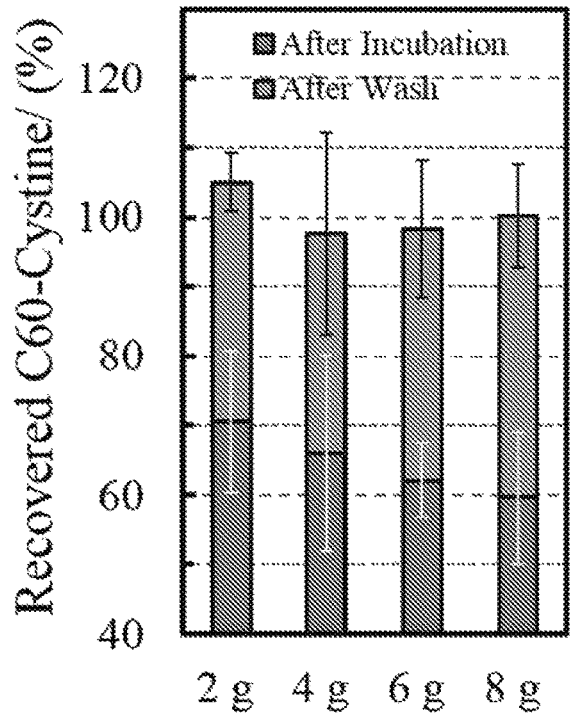
FIG. 10C Wild Sand
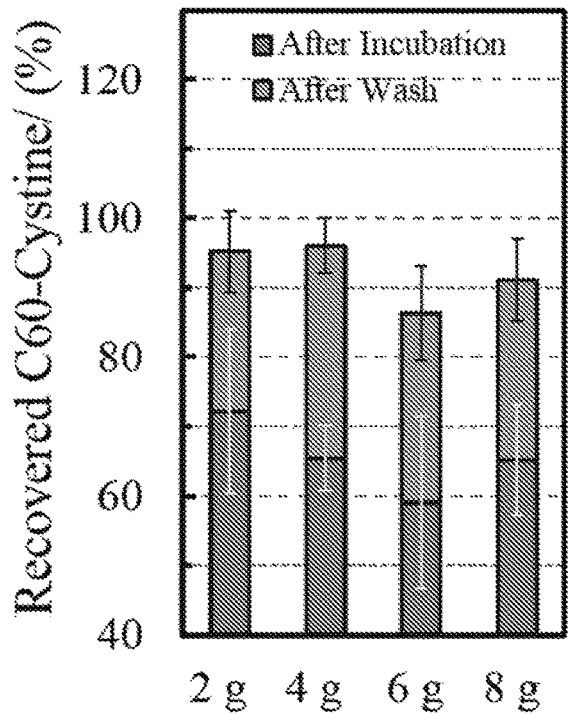
FIG. 10D Natural Soil Differentiation of Live and Dead Microorganisms Radioactive Counting After Wash

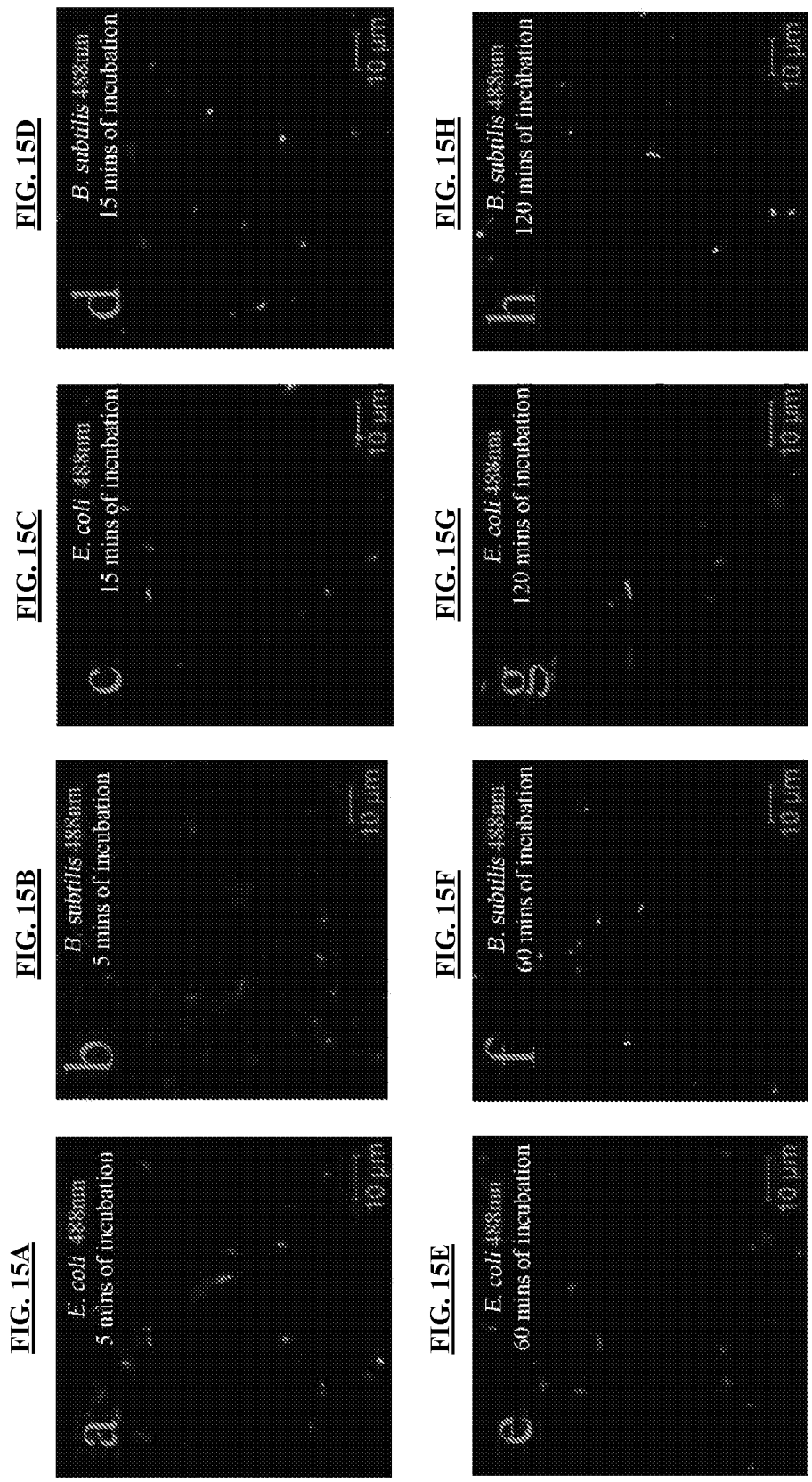

FIG. 16A
FIG. 16B
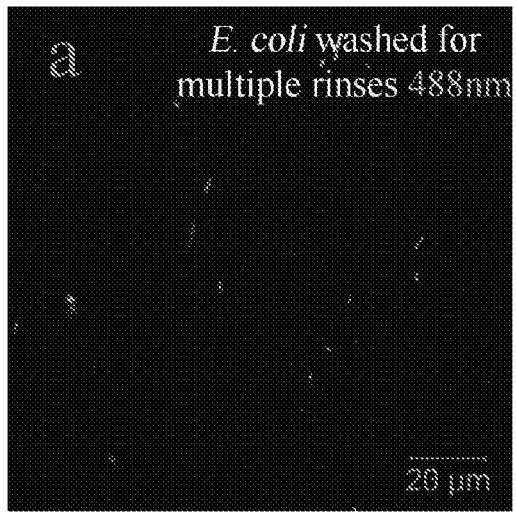
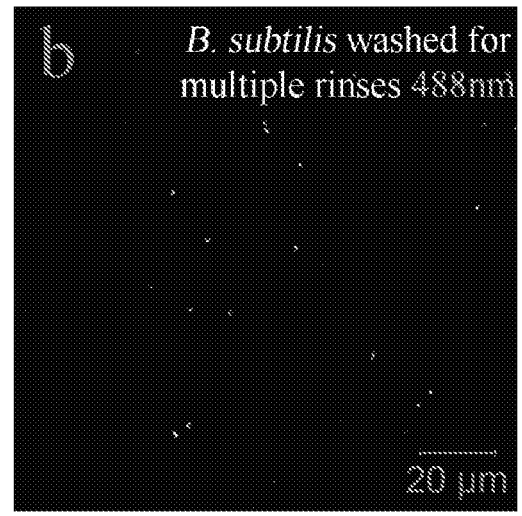
FIG. 17A
FIG. 17B
FIG. 17C
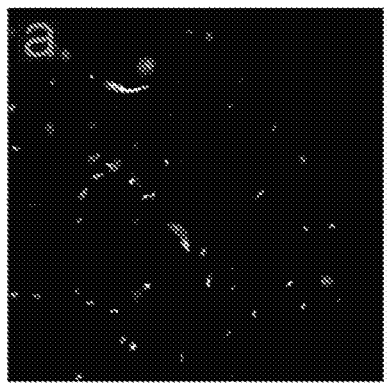
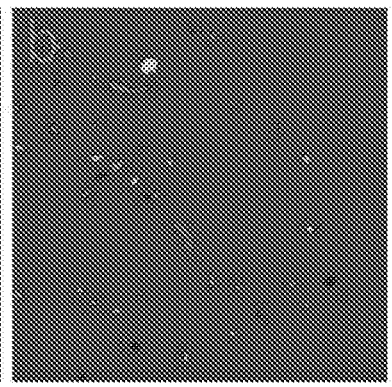
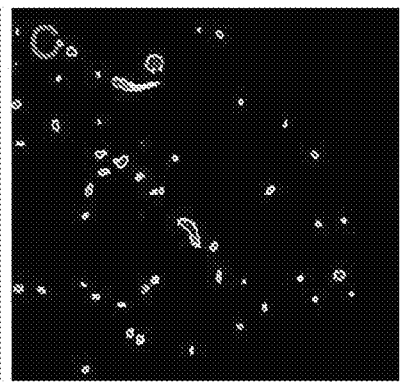

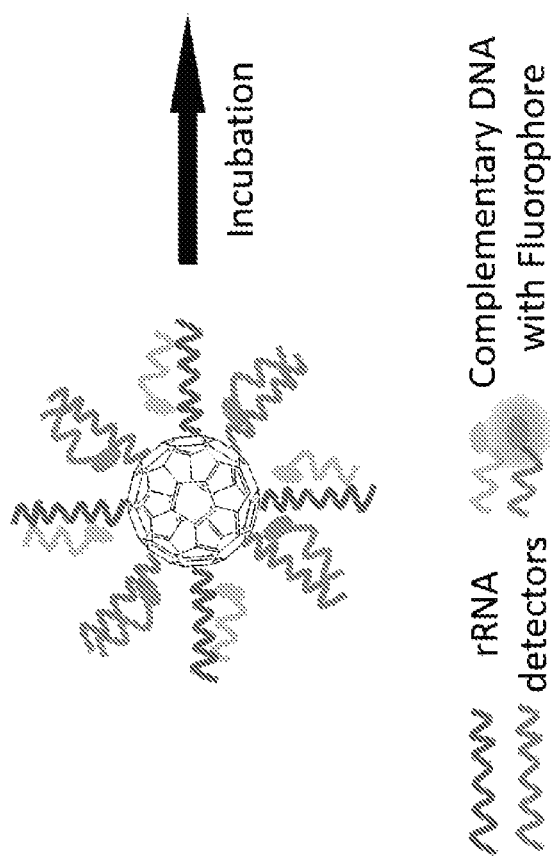
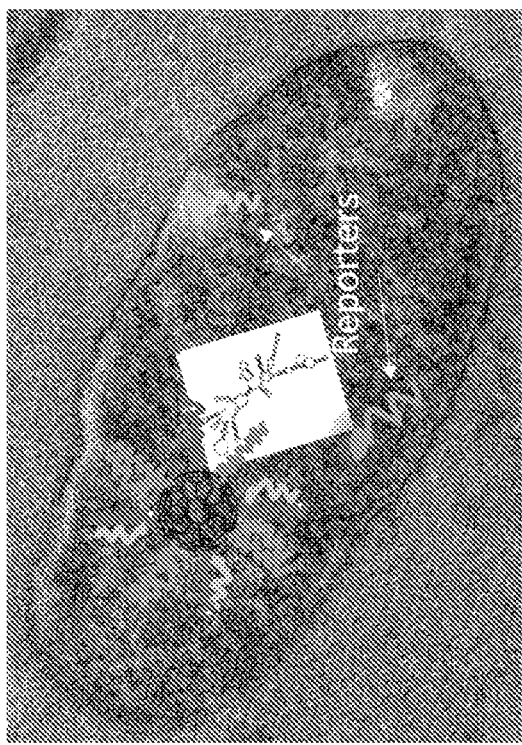
FIG. 20C

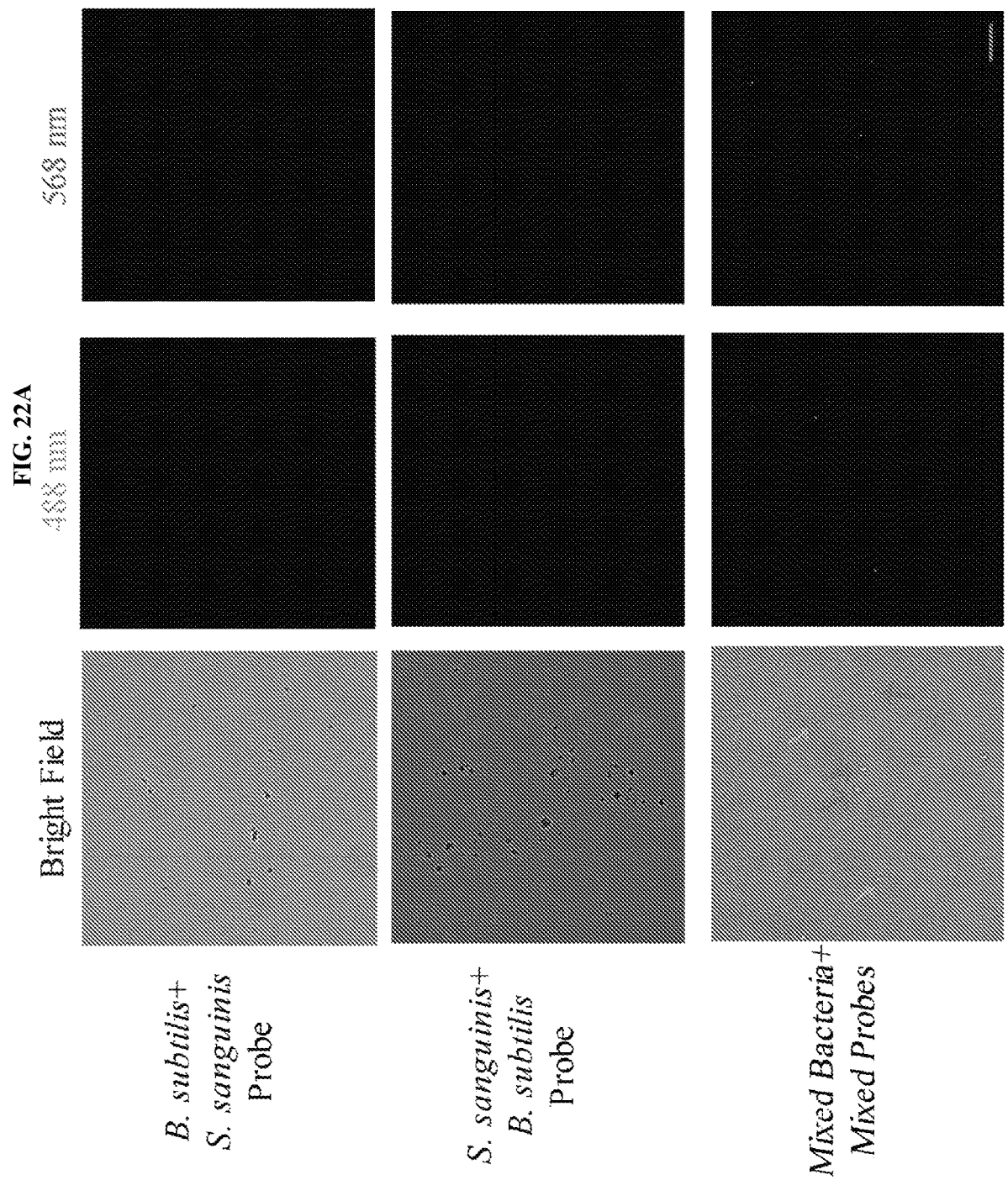

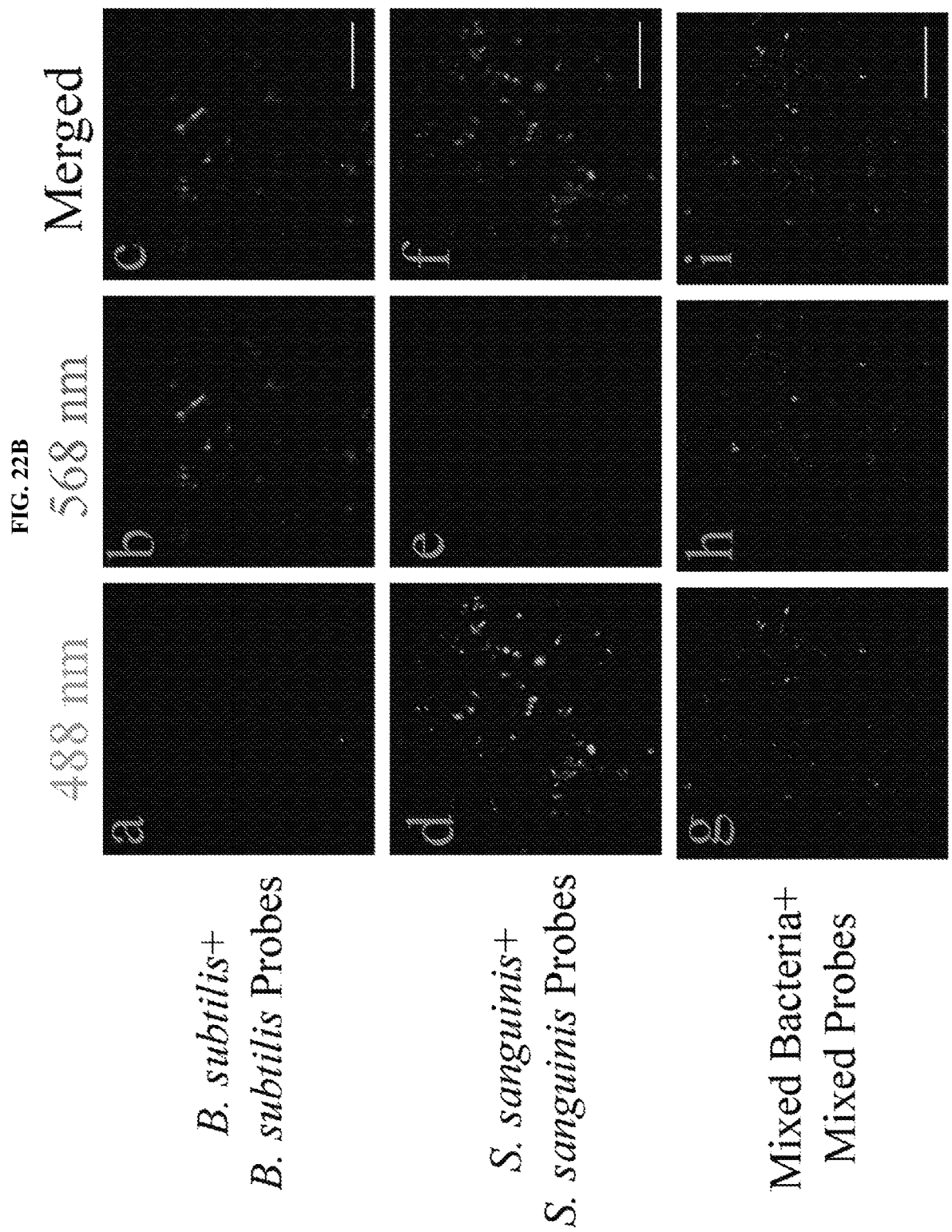

ations, the successful imaging of which is highly dependent on the design of the imaging instruments. Thus, a need still exists to develop probes that allow efficient in situ visualization of microbial density that overcome the problems associated with the currently available technologies.

There is thus a need in the art for probes that allow efficient in situ visualization of microbial presence and density that are non-destructive and non-invasive. Additionally, there remains a need in the art for probes and methods which are capable of differentiating microbial populations quickly, cheaply and effectively. The present invention fulfills these needs.

RAPID IDENTIFICATION OF MICROORGANISMS

CROSS-REFERENCE TO RELATED APPLICATIONS

This application is a 35 U.S.C. § 371 national phase application from, and claims priority to International Application No. PCT/US2016/050122, filed Sep. 2, 2016, which claims priority under 35 U.S.C. § 119(e) to U.S. Provisional Application No. 62/214,687 filed Sep. 4, 2015, and U.S. Provisional Application No. 62/249,098 filed Oct. 30, 2015, all of which applications are incorporated herein by reference in their entireties.

STATEMENT REGARDING FEDERALLY SPONSORED RESEARCH OR DEVELOPMENT

This invention was made with government support under grant number DE-AC02-05CH11231 awarded by the U.S. Department of Energy. The government has certain rights in the invention.

BACKGROUND

Soil hosts most of the biodiversity in the environment, where each cubic centimeter of soil matrix can contain hundreds of thousands of microorganisms that cohabitate in a complex assemblage of mineral and organic matter. The structure and function of microbial communities are dynamic processes that play important and beneficial roles in productivity of ecosystems, including oxygen production, crop growth, bioremediation, carbon sequestration, nitrogen fixation, and water purification. Simultaneously, microbial species may act as pathogens for living organisms. For example, plants from hundreds of different species are killed annually in Australia by *P. cinnamomi*; and grain development, in wheat, is affected by infection of *G. graminis* var. *tritici* in vascular tissue. Therefore, there is a need to develop the probes and assays that enable studying microbial species in their native environment, i.e., in situ imaging. Applications of in situ imaging include, but are not limited to, the insights and understanding of the (i) composition and population of a normal gut microbiome as a function of exposure to antibiotics and/or under environmental stress; (ii) interactions and cross talk between microbes and plant roots in rhizosphere; (iii) localization of endophytes in healthy plant tissues for improved yield; and (iv) profiling of the microbial communities in soil crust for erosion control, water retention, and nutrient cycling.

To meet the requirements of in situ imaging and identification of microorganisms, synthesized probes must (i) penetrate the cell wall and lipid membrane, (ii) be non-sticky to the soil matrix, and (iii) differentiate between living and dead microorganisms. Previously, guanidinium-rich molecular transporters (GR-MoTrs) have been demonstrated to be internalized in different strains of algae by crossing both the cell wall and the lipid membrane; however, it was later discovered that these molecular transporters were sticky to the matrix substrate. Other polymer-based nanoparticles, such as lipofectamine, have also been found to be sticky to the natural environment. Moreover, in some cases, synthesized probes ideally should facilitate radiolabeling to meet the general requirements of in situ imaging. For example, the structure of a microbial community can be imaged with x-ray microtomography and MRI, but these techniques are destructive and do not report biological

BRIEF SUMMARY OF THE INVENTION

The invention provides a method of selectively labeling a specific species of microorganism in a sample, the method comprising:
a) functionalizing a Buckminsterfullerene molecule with one or more RNA oligonucleotides complementary to one or more species specific signature RNA sequences of the microorganism in the sample;
b) hybridizing the one or more RNA oligonucleotides to protecting layers comprising segments of DNA or RNA and a detectable label; and
c) contacting the sample with the functionalized Buckminsterfullerene molecule for a period of time;
wherein, the detectable label is not detected when the protecting layers are hybridized to the one or more RNA oligonucleotides and the detectable label is detected when the protecting layers are not hybridized, thereby selectively labeling a specific species of microorganism in the sample.

In certain embodiments, the one or more species specific signature RNA sequences are 16S rRNA sequences or mRNA sequences. In other embodiments, the one or more RNA oligonucleotides are selected by bioinformatics analysis. In yet other embodiments, the protecting layers are about 75% complementary to the corresponding RNA oligonucleotides. In yet other embodiments, the one or more RNA oligonucleotides are each independently about 80% to a 100% complementary to the corresponding species specific signature RNA sequences. In yet other embodiments, the one or more RNA oligonucleotides each independently comprise about 20 to about 50 individual nucleotides.

In certain embodiments, two or more specific species of microorganisms are labelled simultaneously with different functionalized Buckminsterfullerene molecules specific for each organism, and wherein each different functionalized Buckminsterfullerene comprises a unique detectable label such that each species of microorganism is labelled with a unique detectable label corresponding to that specific species. In other embodiments, the presence or absence of the two or more specific species of microorganisms can be determined by detecting the presence or absence of the corresponding unique detectable label. In other embodiments, the relative abundance of each of the two or more specific species of microorganism is determined by measuring the relative intensity of the two or more unique detectable labels.

In certain embodiments, the two or more specific species of microorganisms are contained in a single mixed sample. In other embodiments, the microorganisms are live microorganisms. In yet other embodiments, the microorganism is selected from the group consisting of bacteria, fungi, archaea and protists.

In certain embodiments, the microorganism is labeled in a medium selected from the group consisting of a solution, an organic matrix and a soil matrix. In other embodiments, the functionalized Buckminsterfullerene molecules are functionalized so that they do not adhere or stick to the medium and can be removed from the medium.

In certain embodiments, the Buckminsterfullerene molecule is selected from the group consisting of C60 Buckminsterfullerene, C70 Buckminsterfullerene and C60-pyrrolidine tris acid Buckminsterfullerene. In certain embodiments, the detectable label is selected from the group consisting of a fluorescent tag, a radioactive isotope, an amino acid, a nucleic acid, and a peptide. In other embodiments, the detectable label is selected from the group consisting of glycine, tryptophan, arginine, cysteine, fBSA, $^{14}C$, $^{125}I$, and cy3/6-FAM In certain embodiments, detectable label is detected using a method selected from the group consisting of autoradiography, fluorescence microscopy, X-ray fluorescence microscopy, UV-vis spectroscopy, TEM and fluorescent spectroscopy.

In certain embodiments, the microorganism internalizes the functionalized Buckminsterfullerene.

In certain embodiments, identification of the microorganism does not require sample fixation.

The invention further provides a method of labeling and identifying a microorganism, the method comprising:
  a) functionalizing a Buckminsterfullerene molecule with a detectable label;
  b) incubating the microorganism with the functionalized Buckminsterfullerene molecule for a period of time.

In certain embodiments, the Buckminsterfullerene molecule is selected from the group consisting of C60 Buckminsterfullerene, C70 Buckminsterfullerene and C60-pyrrolidine tris acid Buckminsterfullerene.

In certain embodiments, the detectable label is selected from the group consisting of a fluorescent tag, a radioactive isotope, an amino acid, a nucleic acid, and a peptide. In other embodiments, the detectable label is selected from the group consisting of glycine, tryptophan, arginine, cysteine, fBSA, $^{14}C$, $^{125}I$, and cy3/6-FAM. In other embodiments, the detectable label is detected using a method selected from the group consisting of autoradiography, fluorescence microscopy, X-ray fluorescence microscopy, UV-vis spectroscopy, TEM and fluorescent spectroscopy.

In certain embodiments, the microorganism internalizes the functionalized Buckminsterfullerene.

In certain embodiments, more than one microorganism is labeled and live microorganisms are differentiated from dead microorganisms. In other embodiments, dead microorganisms internalize more of the functionalized Buckminsterfullerene molecules than living microorganisms.

In certain embodiments, the microorganism does not require sample fixation.

In certain embodiments, the microorganism is selected from the group consisting of bacteria, fungi, archaea and protists.

The invention further provides a method of detecting gene expression in a living microorganism, the method comprising:
  a) functionalizing a Buckminsterfullerene molecule with one or more RNA oligonucleotides complementary to one or more mRNA segments of interest corresponding to a gene of interest;
  b) hybridizing the one or more RNA oligonucleotides to one or more complementary protecting layers comprising segments of DNA or RNA and a detectable label; and
  c) contacting a sample containing a living microorganism with the functionalized Buckminsterfullerene molecule for a period of time;
  wherein, the detectable label is not detected when the protecting layers are hybridized to the one or more RNA oligonucleotides and the detectable label is detected when the protecting layers are not hybridized, thereby detecting gene expression in a living microorganism.

The invention also provides a method of inhibiting gene expression in a living microorganism, the method comprising:
  a) functionalizing a Buckminsterfullerene molecule with one or more RNA oligonucleotides complementary to one or more mRNA segments of interest corresponding to a gene of interest;
  b) hybridizing the one or more RNA oligonucleotides to one or more complementary protecting layers comprising segments of DNA or RNA and optionally a detectable label; and
  c) contacting the sample with the functionalized Buckminsterfullerene molecule for a period of time;
  wherein the one or more RNA oligonucleotides hybridize with free mRNA in the cytoplasm, preventing transcription and gene expression; and
  wherein, the detectable label, if present, is not detected when the protecting layers are hybridized to the one or more RNA oligonucleotides and the detectable label is detected when the protecting layers are not hybridized.

In certain embodiments, the one or more RNA oligonucleotides are selected by bioinformatics analysis. In certain embodiments, the protecting layers are about 75% complementary to the corresponding RNA oligonucleotides. In certain embodiments, the one or more RNA oligonucleotides are each independently about 80% to a 100% complementary to the corresponding species specific signature RNA sequences. In certain embodiments, the one or more RNA oligonucleotides each independently comprise about 20 to about 50 individual nucleotides. In certain embodiments, the one or more RNA oligonucleotides are siRNA oligonucleotides.

In certain embodiments, the Buckminsterfullerene molecule is selected from the group consisting of C60 Buckminsterfullerene, C70 Buckminsterfullerene and C60-pyrrolidine tris acid Buckminsterfullerene.

In certain embodiments, the detectable label is from the group consisting of a fluorescent tag, a radioactive isotope, an amino acid, a nucleic acid, and a peptide. In other embodiments, the detectable label is selected from the group consisting of glycine, tryptophan, arginine, cysteine, fBSA, $^{14}C$, $^{125}I$, and cy3/6-FAM. In yet other embodiments, the detectable label is detected using a method selected from the group consisting of autoradiography, fluorescence microscopy, X-ray fluorescence microscopy, UV-vis spectroscopy, TEM and fluorescent spectroscopy.

In certain embodiments, the detection and inhibition methods do not require sample fixation.

In certain embodiments, the microorganism is selected from the group consisting of bacteria, fungi, archaea and protists.

In certain embodiments, the microorganism internalizes the functionalized Buckminsterfullerene.

In certain embodiments, biological processes can be monitored and profiled by dynamic visualization of mRNA expression.

The invention further provides a system for labelling, identifying and differentiating living microorganisms of different species within a sample, the system comprising:
  a) one or more source wells and one or more sink wells, wherein the source wells and the sink wells are in fluidic communication with each other;
  b) one or more functionalized Buckminsterfullerene molecules for each species of microorganism in the sample, wherein the Buckminsterfullerene molecules are functionalized with one or more RNA oligonucleotides complementary to one or more species specific signature RNA sequences of the microorganisms in the sample, wherein the one or more RNA oligonucleotides are hybridized to protecting layers comprising segments of DNA or RNA and a detectable label;
  wherein, the detectable label is not detected when the protecting layers are hybridized to the one or more RNA oligonucleotides and the detectable label is detected when the protecting layers are not hybridized; and wherein, each sink well comprises a different type of functionalized Buckminsterfullerene molecule, bound to a different detectable label, each corresponding to a different microorganism species; and wherein the microorganisms are labeled, identified and differentiated by:
  a) placing a sample comprising one or more different species of microorganisms in the source well;
  b) allowing the microorganisms to migrate to the one or more sink wells, coming in contact with and internalizing the one or more functionalized Buckminsterfullerene molecules; and
  wherein the microorganisms emit a signal if in contact with a Buckminsterfullerene molecule comprising an RNA oligonucleotide which matches a species specific signature RNA sequence within the microorganism.

In certain embodiments, the number of sink wells is equivalent to the number of microorganism species of interest within the sample. In other embodiments, each sink well further comprises a microbial attractant which attracts the microorganism species of interest matching the functionalized Buckminsterfullerene molecule present in that same sink well. In other embodiments, the microbial attractant is a nutrient, mineral or environmental condition meant to draw the microorganism of interest to the sink well. In yet other embodiments, the microbial attractant is one or more conditions selected from the group consisting of a sugar gradient, a protein gradient, a metal ion gradient, a temperature gradient, a salinity gradient, a light gradient and a specific wavelength of light.

In certain embodiments, the functionalized Buckminsterfullerene molecules are printed into the one or more sink wells.

In certain embodiments, the one or more species specific signature RNA sequences are 16S rRNA sequences or mRNA sequences. In certain embodiments, the one or more RNA oligonucleotides are selected by bioinformatics analysis. In certain embodiments, the protecting layers are about 75% complementary to the corresponding RNA oligonucleotides. In certain embodiments, the one or more RNA oligonucleotides are each independently about 80% to a 100% complementary to the corresponding species specific signature RNA sequences. In certain embodiments, the one or more RNA oligonucleotides each independently comprise about 20 to about 50 individual nucleotides. In certain embodiments, the microorganisms are selected from the group consisting of bacteria, fungi, archaea and protists.

In certain embodiments, the Buckminsterfullerene molecules are selected from the group consisting of C60 Buckminsterfullerene, C70 Buckminsterfullerene and C60-pyrrolidine tris acid Buckminsterfullerene.

In certain embodiments, the detectable labels are selected from the group consisting of fluorescent tags, radioactive isotopes, amino acids, nucleic acids, and peptides. In certain embodiments, the detectable labels are selected from the group consisting of glycine, tryptophan, arginine, cysteine, fBSA, $^{14}C$, $^{125}I$, and cy3/6-FAM. In certain embodiments, the detectable labels are detected using a method selected from the group consisting of autoradiography, fluorescence microscopy, X-ray fluorescence microscopy, UV-vis spectroscopy, TEM and fluorescent spectroscopy.

In certain embodiments, identification of microorganisms does not require sample fixation.

In certain embodiments, the system further comprises an imaging device which can observe and record the signal emitted from each sink well.

In certain embodiments, the system can determine the presence or absence of the one or more microorganism species of interest. In certain embodiments, the system can determine the relative abundance of each of the one or more microorganism species of interest.

The invention further provides a functionalized Buckminsterfullerene composition comprising:
  C60-pyrrolidine tris acid Buckminsterfullerene; and
  one or more detectable labels selected from the group consisting of a fluorescent tag, a radioactive isotope, an amino acid, a nucleic acid, and a peptide.

In certain embodiments, the composition further comprises one or more non-coding RNA oligonucleotides. In certain embodiments, the one or more RNA oligonucleotides each independently comprise about 20 to about 50 individual nucleotides.

In certain embodiments, the composition further comprises protecting layers, wherein the protecting layers are segments of DNA or RNA which can be hybridized to the one or more RNA oligonucleotides. In certain embodiments, the protecting layers are about 75% complementary to the corresponding RNA oligonucleotides. In certain embodiments, the one or more detectable labels are bound to the protecting layers.

In certain embodiments, the one or more detectable labels are selected from the group consisting of a fluorescent tag, a radioactive isotope, an amino acid, a nucleic acid, and a peptide. In other embodiments, the one or more detectable labels are selected from the group consisting of glycine, tryptophan, arginine, cysteine, fBSA, $^{14}C$, $^{125}I$, and cy3/6-FAM

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 2A-2F illustrate cellular uptake of fBSA labelled C60-pyrrolidine tris acid by E. coli and B. subtilis monitored by Confocal Laser Scanning Microscopy. FIGS. 2A and 2B, fBSA-C60 pyrrolidine tris acid uptake by E. coli (FIG. 2A) and B. subtilis (FIG. 2B) visualized by exciting fBSA fluorescence using the 488 nm laser. FIGS. 2C and 2D are bright field (BF) images of the microorganisms. FIGS. 2E and 2F are merged fluorescence and BF images indicate that the fluorescent signals co-localize with the presence of the microorganisms indicating interactions between fBSA labelled C60-pyrrolidine tris acid and microorganisms.

FIGS. 4A and 4B illustrate $^{14}$C60-pyrrolidine tris acid uptake by *E. coli* (FIG. 4A) and *B. subtilis* (FIG. 4B). FIGS. 4C and 4D $^{125}$I-C60-pyrrolidine tris acid uptake by *E. coli* (FIG. 4C) and *B. subtilis* (FIG. 4D).

FIGS. 5A-5D illustrate the non-stickiness of C60-pyrrolidine tris acid to multiple matrices, with increasing weights, monitored by Ultraviolet (UV) light absorption. The hatched regions indicate immediate recovery following incubation and the filled regions indicate recovery following multiple washes. FIGS. 5A-5D illustrate recovery of C60-pyrrolidine tris acid from alumina (FIG. 5A), VWR sand (FIG. 5B), wild sand (FIG. 5C), and natural soil (FIG. 5D). The results indicate that C60-pyrrolidine tris acid remains non-sticky to the various matrices. The total recovery of C60-pyrrolidine tris acid is approximately 100%.

FIG. 7 illustrates the non-stickiness of radiotracers $^{14}$C- and $^{125}$I-labeled C60-pyrrolidine tris acid, on several matrices, monitored by Autoradiography following several washes. The left column shows the background radiation. The middle and right columns indicate that neither β-radiation nor γ-radiation are detected by autoradiography after several washes, indicating C60-pyrrolidine tris acid is not sticky to multiple matrices

FIGS. 10A-10D illustrate the non-stickiness of C60-pyrrolidine tris-Cysteine to multiple soil matrices monitored by Ultraviolet light absorption. Recovery of C60-Cysteine from alumina (FIG. 10A), VWR sand (FIG. 10B), Wild Sand (FIG. 10C) and Natural Soil (FIG. 10D) of different mass indicate that the newly synthesized C60-pyrrolidine tris-Cysteine remains non-sticky to multiple matrices. The hatched regions indicate immediate recovery following incubation, and the filled regions indicate recovery following multiple washes. The total recovery of C60-pyrrolidine tris acid is approximately 100%.

FIGS. 12A and 12B illustrate autofluorescence background for *B. subtilis* (FIG. 12A) and *E. coli* (FIG. 12B) with 488 nm excitation. FIGS. 12C and 12D are bright field images of *B. subtilis* (FIG. 12C) and *E. coli* (FIG. 12D) indicate presence of microorganisms. FIGS. 12E-12F are merged bright field and autofluorescence provides additional evidence for absence of any signal.

FIGS. 15A-15H illustrate time course studies for uptake of C60-pyrrolidine tris acid-fBSA, monitored by confocal microscopy, for *E. coli* (A, C, E, and F) or *B. Subtilis* (B, D, F, and H) indicate time-dependency.

FIGS. 16A-16B illustrate retention of C60-pyrrolidine tris acid-fBSA, monitored by confocal microscopy, after 6 rinses for (FIG. 16A) *E. coli* and (FIG. 16B) *B. Subtilis*.

FIGS. 17A-17C provide steps in quantification of fluorescent images captured through confocal microscopy for Tables 1 and 2: (FIG. 17A) Enhanced image for visualization; (FIG. 17B) segmented microbes followed by connected components; and (FIG. 17C) extracted boundaries for each segmented microbe.

FIGS. 20A-20C are drawings illustrating the use of C60 molecules functionalized with rRNA reporter RNA complexes for the labeling of specific bacterium. FIG. 20A is a schematic illustrating an exemplary method of decorating C60 with rRNA reporters which allows for visualization of each microbe at a specific excitation frequency. FIG. 20B illustrates the functionalization and internalization of the functionalized C60 molecules into a bacterium. FIG. 20C illustrates the internalization of the functionalized C60 molecules into a bacterium.

FIGS. 22A-22B are a series of images illustrating the differentiation of *B. subtilis* and *S. sanguinis* using the compositions of the invention as monitored by super resolution microscopy. *B. subtilis* incubated with *B. subtilis* probe complex shows no fluorescent signal at 488 nm excitation frequency, but fluoresces at 568 nm excitation frequency. *S. sanguinis* incubated with *S. sanguinis* probe complex shows fluorescent signal at 488 nm excitation frequency, and no fluorescence signal at 568 nm excitation frequency. Mixed bacteria and probe complexes indicate that each bacterium can be visualized at its corresponding excitation frequency. Scale bar is 10 µm.

DETAILED DESCRIPTION OF THE INVENTION

Figure 1:
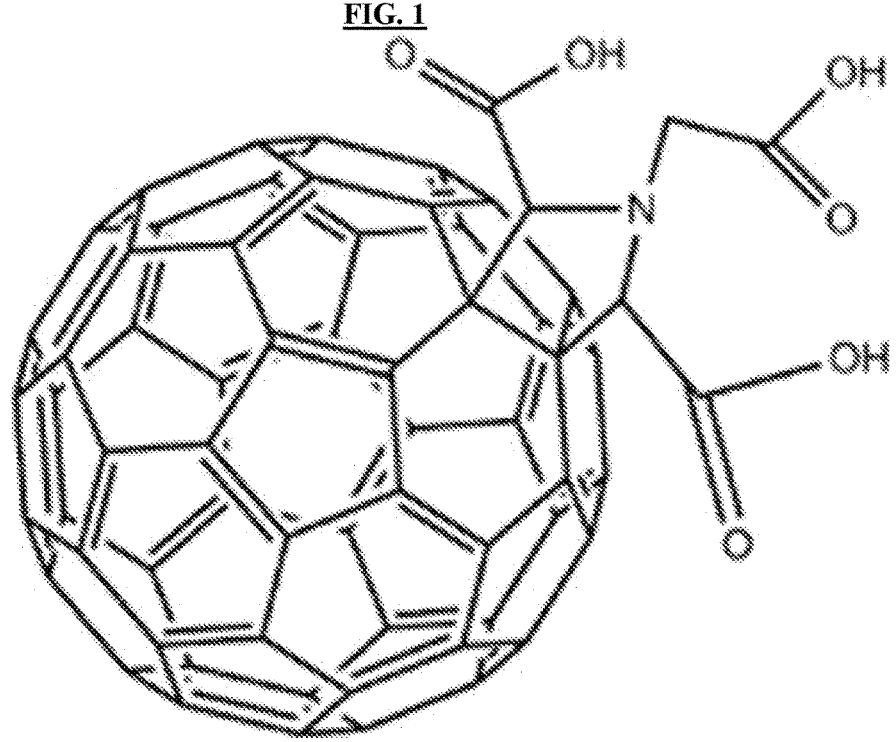
FIG. 1 is a schematic of C60-pyrrolidine tris acid, which indicates that C60-pyrrolidine tris acid has three potential decoration sites while maintaining the carbon cage structure intact.

The invention relates to the unexpected discovery that functionalized Buckyballs (e.g., C60-pyrrolidine tris acid) are a versatile platform for internalizing chemical payloads into microorganisms. In certain embodiments, functionalized Buckyballs can be used to transport a detectable label into a living microorganism. In certain embodiments, the Buckyballs can transport detectable label complexes which are able to discriminate between different microorganisms and selectively emit a signal only once inside a specific organism. In other embodiments, the invention includes devices and methods which utilize the functionalized Buckyballs of the invention to determine microbial density and/or differentiate between different species of microorganism in a sample.

Definitions

As used herein, each of the following terms has the meaning associated with it in this section.

As used herein, unless defined otherwise, all technical and scientific terms generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, from the specified value, as such variations are appropriate to perform the disclosed methods.

As used herein, the term "bacteria" means a large domain of prokaryotic microorganisms. Typically a few micrometres in length, bacteria have a wide range of shapes, ranging from spheres to rods and spirals. There are broadly speaking two different types of cell wall in bacteria, called Gram-positive and Gram-negative. Gram-positive bacteria possess a thick cell wall containing many layers of peptidoglycan and teichoic acids. In contrast, Gram-negative bacteria have a relatively thin cell wall consisting of a few layers of peptidoglycan surrounded by a second lipid membrane containing lipopolysaccharides and lipoproteins. Most bacteria have the Gram-negative cell wall, and only the Firmicutes and Actinobacteria have the alternative Gram-positive arrangement.

As used herein, the terms "bacterial pathogen" or "pathogenic bacteria" mean a bacterium that causes disease. Examples of pathogenic bacteria which can be detected and monitored by the disclosed methods and compositions include, without limitation, any one or more of (or any combination of) *Acinetobacter baumanii*, *Actinobacillus* sp., *Actinomycetes*, *Actinomyces* sp. (such as *Actinomyces israelii* and *Actinomyces naeslundii*), *Aeromonas* sp. (such as *Aeromonas hydrophila*, *Aeromonas veronii* biovar *sobria* (*Aeromonas sobria*), and *Aeromonas caviae*), *Anaplasma phagocytophilum*, *Alcaligenes xylosoxidans*, *Acinetobacter baumanii*, *Actinobacillus actinomycetemcomitans*, *Bacillus* sp. (such as *Bacillus anthracis*, *Bacillus cereus*, *Bacillus subtilis*, *Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae*, *Bifidobacterium* sp., *Bordetella* sp. (such as *Bordetella pertussis*, *Bordetella parapertussis*, and *Bordetella bronchiseptica*), *Borrelia* sp. (such as *Borrelia recurrentis*, and *Borrelia burgdorferi*), *Brucella* sp. (such as *Brucella abortus*, *Brucella canis*, *Brucella melintensis* and *Brucella suis*), *Burkholderia* sp. (such as *Burkholderia pseudomallei* and *Burkholderia cepacia*), *Campylobacter* sp. (such as *Campylobacter jejuni*, *Campylobacter coli*, *Campylobacter lari* and *Campylobacter fetus*), *Capnocytophaga* sp., *Cardiobacterium hominis*, *Chlamydia trachomatis*, *Chlamydophila pneumoniae*, *Chlamydophila psittaci*, *Citrobacter* sp. *Coxiella burnetii*, *Corynebacterium* sp. (such as, *Corynebacterium diphtheriae*, *Corynebacterium jeikeum* and *Corynebacterium*), *Clostridium* sp. (such as *Clostridium perfringens*, *Clostridium dificile*, *Clostridium botulinum* and *Clostridium tetani*), *Eikenella corrodens*, *Enterobacter* sp. (such as *Enterobacter aerogenes*, *Enterobacter agglomerans*, *Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), *Erysipelothrix rhusiopathiae*, *Eubacterium* sp., *Francisella tularensis*, *Fusobacterium nucleatum*, *Gardnerella vaginalis*, *Gemella morbillorum*, *Haemophilus* sp. (such as *Haemophilus influenzae*, *Haemophilus ducreyi*, *Haemophilus aegyptius*, *Haemophilus parainfluenzae*, *Haemophilus haemolyticus* and *Haemophilus parahaemolyticus*, *Helicobacter* sp. (such as *Helicobacter pylori*, *Helicobacter cinaedi* and *Helicobacter fennelliae*), *Kingella kingii*, *Klebsiella* sp. (such as *Klebsiella pneumoniae*, *Klebsiella granulomatis* and *Klebsiella* oxytoca), *Lactobacillus* sp., *Listeria monocytogenes*, *Leptospira interrogans*, *Legionella pneumophila*, *Leptospira interrogans*, *Peptostreptococcus* sp., *Moraxella catarrhalis*, *Morganella* sp., *Mobiluncus* sp., *Micrococcus* sp., *Mycobacterium* sp. (such as *Mycobacterium leprae, Mycobacterium tuberculosis, Mycobacterium intracellulare, Mycobacterium avium, Mycobacterium bovis*, and *Mycobacterium marinum*), *Mycoplasm* sp. (such as *Mycoplasma pneumoniae, Mycoplasma hominis*, and *Mycoplasma genitalium*), *Nocardia* sp. (such as *Nocardia asteroides, Nocardia cyriacigeorgica* and *Nocardia brasiliensis*), *Neisseria* sp. (such as *Neisseria gonorrhoeae* and *Neisseria meningitidis*), *Pasteurella multocida, Plesiomonas shigelloides. Prevotella* sp., *Porphyromonas* sp., *Prevotella melaninogenica, Proteus* sp. (such as *Proteus vulgaris* and *Proteus mirabilis*), *Providencia* sp. (such as *Providencia alcalifaciens, Providencia rettgeri* and *Providencia stuartii*), *Pseudomonas aeruginosa, Propionibacterium acnes, Rhodococcus equi, Rickettsia* sp. (such as *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* sp., *Serratia marcescens, Stenotrophomonas maltophilia, Salmonella* sp. (such as *Salmonella enterica, Salmonella typhi, Salmonella paratyphi, Salmonella enteritidis, Salmonella choleraesuis* and *Salmonella typhimurium*), *Serratia* sp. (such as *Serratia marcesans* and *Serratia liquifaciens*), *Shigella* sp. (such as *Shigella dysenteriae, Shigellaf lexneri, Shigella boydii* and *Shigella sonnei*), *Staphylococcus* sp. (such as *Staphylococcus aureus, Staphylococcus epidermidis, Staphylococcus hemolyticus, Staphylococcus sapmphyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A streptococci, *Streptococcus pyogenes*, Group B streptococci, *Streptococcus agalactiae*, Group C streptococci, *Streptococcus anginosus, Streptococcus equismilis*, Group D streptococci, *Streptococcus bovis*, Group F streptococci, and *Streptococcus anginosus* Group G streptococci), *Spirillum minus, Streptobacillus moniliformi, Treponema* sp. (such as *Treponema carateum, Treponema petenue, Treponema pallidum* and *Treponema endemicum, Tropheryma whippelii, Ureaplasma urealyticum, Veillonella* sp., *Vibrio* sp. (such as *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio furnisii*), *Yersinia* sp. (such as *Yersinia enterocolitica, Yersinia pestis*, and *Yersinia pseudotuberculosis*) and *Xanthomonas maltophilia* among others.

As used herein, the terms "Buckminsterfullerene" or "Buckyball" mean a spherical fullerene molecule with the formula C60 or other spherical fullerene molecules (e.g., C70). These spherical fullerene molecules have a cage-like fused-ring structure (truncated icosahedron). For example, C60 is made of twenty hexagons and twelve pentagons, with a carbon atom at each vertex of each polygon and a bond along each polygon edge. Buckminsterfullerene is the most common naturally occurring fullerene molecule, as it can be found in small quantities in soot. Solid and gaseous forms of the molecule have been detected in deep space.

As used herein, the term "contacting means placement in direct physical association, including both a solid and liquid form. Contacting an agent with a cell can occur in vitro by adding the agent to isolated cells or in vivo by administering the agent to a subject.

As used herein, the term "fungus" means living, single-celled and multicellular organisms belonging to the kingdom Fungi. Most species are characterized by a lack of chlorophyll and presence of chitinous cell walls, and some fungi may be multinucleated. The methods disclosed herein can be used to detect and identify antigens associated with particular fungi.

The term "fungal pathogen" means a fungus that causes disease. Examples of fungal pathogens which can be detected and monitored by the disclosed methods and compositions include, without limitation, any one or more of (or any combination of) *Trichophyton rubrum, T. mentagrophytes, Epidermophyton floccosum, Microsporum canis, Pityrosporum orbiculare (Malassezia furfur), Candida* sp. (such as *Candida albicans*), *Aspergillus* sp. (such as *Aspergillus fumigatus, Aspergillus flavus* and *Aspergillus clavatus*), *Cryptococcus* sp. (such as *Cryptococcus neoformans, Cryptococcus gattii, Cryptococcus laurentii* and *Cryptococcus albidus*), *Histoplasma* sp. (such as *Histoplasma capsulatum*), *Pneumocystis* sp. (such as *Pneumocystis jirovecii*), and *Stachybotrys* (such as *Stachybotrys chartarum*).

As used herein, "hybridization" means to form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of non-limiting hybridization conditions:

Very High Stringency (Detects Sequences that Share at Least 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (Detects Sequences that Share at Least 80% Identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Detects Sequences that Share at Least 60% Identity)
Hybridization: 6×SSC at RT to 55° C. for 16-20 hours Wash at least twice: 2×-3×SSC at RT to 55° C. for 20-30 minutes each.

The term "label" as used herein means a detectable compound or composition that is conjugated directly or indirectly to another molecule, such as an antibody or a protein, to facilitate detection of that molecule. Specific, non-limiting examples of labels include fluorescent tags, enzymatic linkages (such as horseradish peroxidase), radioactive isotopes (for example $^{14}C$, $^{32}P$, $^{125}I$, $^{3}H$ isotopes and the like) and particles such as colloidal gold. In some examples, a molecule is labeled with a radioactive isotope, such as $^{14}C$, $^{32}P$, $^{125}I$, $^{3}H$ isotope. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998), Harlow & Lane (Antibodies, *A Laboratory Manual*, Cold Spring Harbor Publications, New York, 1988).

The term "microorganism" as used herein means a single-celled, or unicellular, organism which include bacteria, fungi, archaea or protists, but not viruses and prions (which are generally classified as non-living). Microorganisms that cause disease in a host are known as pathogens.

The term "Nanoparticle" as used herein means a microscopic particle whose size is measured in nanometers (nm). It is defined as a particle that does not have a dimension >1000 nm, such as having a size between about 10 and about 1000 nm, for example, between about 10 and about 100 nm, between 100 and about 500 nm, or between about 500 and about 1000 nm. Nanoparticles are effectively a bridge between bulk materials and atomic or molecular structures. A bulk material should have constant physical properties regardless of its size, but at the nano-scale this is often not the case. Size-dependent properties are observed such as quantum confinement in semiconductor particles, surface plasmon resonance in some metal particles and superparamagnetism in magnetic materials. Semi-solid and soft nanoparticles have been manufactured. A prototype nanoparticle of semi-solid nature is the liposome.

At the small end of the size range, nanoparticles are often referred to as clusters. Metal, dielectric, and semiconductor nanoparticles have been formed, as well as hybrid structures (e.g., core-shell nanoparticles). Nanospheres, nanorods, and nanocups are just a few of the shapes that have been grown. Semiconductor quantum dots and nanocrystals are types of nanoparticles. Such nanoscale particles are used in biomedical applications as drug carriers or imaging agents.

Nanoparticle characterization is necessary to establish understanding and control of nanoparticle synthesis and applications. Characterization is done by using a variety of different techniques, mainly drawn from materials science. Common techniques are electron microscopy (transmission or scanning, abbreviated TEM or SEM respectively), atomic force microscopy (AFM), dynamic light scattering (DLS), x-ray photoelectron spectroscopy (XPS), powder x-ray diffractometry (XRD), and Fourier transform infrared spectroscopy (FTIR).

The term "nucleic acid" as used herein means a deoxyribonucleotide or ribonucleotide polymer in either single or double stranded form, and unless otherwise limited, encompassing analogs of natural nucleotides that hybridize to nucleic acids in a manner similar to naturally occurring nucleotides. The term "nucleotide" includes, but is not limited to, a monomer that includes a base (such as a pyrimidine, purine or synthetic analogs thereof) linked to a sugar (such as ribose, deoxyribose or synthetic analogs thereof), or a base linked to an amino acid, as in a peptide nucleic acid. A nucleotide is one monomer in a polynucleotide. A nucleotide sequence refers to the sequence of bases in a polynucleotide.

A "target nucleic acid" (such as a target 16S rRNA, miRNA, or target mRNA) is a defined region or particular portion of a nucleic acid molecule, for example a small non-coding RNA (such as an miRNA, siRNA, or piRNA) or mRNA of interest. Where the target nucleic acid sequence is a target miRNA or a target mRNA, such a target can be defined by its specific sequence or function; by its gene or protein name; or by any other means that uniquely identifies it from among other nucleic acids.

In some examples, alterations of a target nucleic acid sequence (e.g., an miRNA, siRNA, piRNA, or an mRNA) are "associated with" a disease or condition. That is, detection of the target nucleic acid sequence can be used to infer the status of a sample with respect to the disease or condition. For example, the target nucleic acid sequence can exist in two (or more) distinguishable forms, such that a first form correlates with absence of a disease or condition and a second (or different) form correlates with the presence of the disease or condition. The two different forms can be qualitatively distinguishable, such as by nucleotide polymorphisms or mutation, and/or the two different forms can be quantitatively distinguishable, such as by the number of copies of the target nucleic acid sequence that are present in a sample.

As used herein, the term "probe" means a nucleic acid molecule or peptide capable of detecting a target. In some examples, a probe includes a detectable label.

"RNA (ribonucleic acid)" as used herein is a long chain polymer which consists of nucleic acids joined by 3'-5' phosphodiester bonds. The repeating units in RNA polymers are four different nucleotides, each of which comprises one of the four bases, adenine, guanine, cytosine, and uracil bound to a ribose sugar to which a phosphate group is attached. In general, DNA is transcribed to RNA by an RNA polymerase. RNA transcribed from a particular gene contains both introns and exons of the corresponding gene; this RNA is also referred to as pre-mRNA. RNA splicing subsequently removes the intron sequences and generates a messenger RNA (mRNA) molecule, which can be translated into a polypeptide. Triplets of nucleotides (referred to as codons) in an mRNA molecule code for each amino acid in a polypeptide, or for a stop signal.

Another form of RNA is small non-coding RNA, including microRNA (miRNA), which are single-stranded RNA molecules that regulate gene expression. miRNAs are generally about 18-25 nucleotides in length. microRNAs typically modulate gene expression (e.g., increase or decrease translation) by promoting cleavage of target mRNAs or by blocking translation of the cellular transcript, miRNAs are processed from primary transcripts known as pri-miRNA to short stem-loop structures called precursor (pre)-miRNA and finally to functional, mature miRNA. Mature miRNA molecules are partially complementary to one or more messenger RNA molecules, and their primary function is to down-regulate gene expression. miRNA sequences are publicly available. For example, miRBase (mirbase.org) includes a searchable database of annotated miRNA sequences. miRNA sequences are also available through other databases known to one of ordinary skill in the art, including the National Center for Biotechnology Information (ncbi.nlm.nih.gov).

"Small non-coding RNA" means any non-coding RNA of about 60 nucleotides or less. Small (or short) non-coding RNAs include microRNA (miRNA; above). Other small non-coding RNAs include small interfering RNA (siRNA), which are about 19-23 nucleotides in length. siRNAs are double-stranded nucleic acid molecules that modulate gene expression through the RNAi pathway. siRNA molecules generally have 2-nucleotide overhangs on each 3' end. However, siRNAs can also be blunt ended. Generally, one strand of a siRNA molecule is at least partially complementary to a target nucleic acid, such as a target mRNA. siRNAs are also referred to as "small inhibitory RNAs" or "short inhibitory RNAs." As used herein, siRNA molecules need not be limited to those molecules containing only RNA, but further encompasses chemically modified nucleotides and non-nucleotides having RNAi capacity or activity. In an example, a siRNA molecule is one that reduces or inhibits the biological activity or expression of mRNA.

Additional small non-coding RNAs include Piwi-interacting RNA (piRNA), which are about 25-30 nucleotides in length and bind Piwi proteins. piRNAs are involved in germ cell development, stem cell self-renewal, and retrotansoposon silencing. Transcription initiation RNAs (tiRNAs) are about 18 nucleotides in length. They are generally found downstream of transcriptional start sites and are involved in regulating transcription of protein-coding genes by targeting epigenetic silencing complexes. Centromere repeat associated small interacting RNA (crasiRNA) are about 34-42 nucleotides in length and are processed from longer dsRNAs. They are involved in recruitment of heterochromatin and/or centromeric proteins. Another type of small non-coding RNA is telomere-specific small RNA (tel-siRNA), which are about 24 nucleotides in length and are 2'-O-methylated at their 3' end. They are involved in epigenetic regulation.

The term "sample" as used herein means a biological specimen containing DNA (for example, genomic DNA or cDNA), RNA (including mRNA or miRNA), protein, or combinations thereof, in some examples obtained from a subject. Examples include, but are not limited to cells, cell lysates, chromosomal preparations, peripheral blood, urine, saliva, tissue biopsy, surgical specimen, bone marrow, amniocentesis samples, and autopsy material. In one example, a sample includes RNA, such as mRNA.

The following abbreviations are used herein:
CNTs carbon nanotubes
DMF dimethylformamide
EDC 1-(3-dimethylaminopropyl)-3-ethylcarbodiimide hydrochloride
fBSA fluorescent bovine serum albumin
GR-MoTrs guanidinium-rich molecular transporters
mRNA messenger RNA
MES 2-(N-morpholino)ethaneosulfonic acid
NHS N-hydroxysuccinimide
PEI poly(ethylenimine)
PEG polyethylene glycerol
PI propidium iodide
PLGA poly(lactic-co-glycolic acid)
rRNA ribosomal RNA
siRNA small interfering RNA
TEM transmission electron microscopy
UV ultraviolet
rcf relative centrifugal force
Compositions The invention provides compositions capable of entering a microorganism comprising one or more functionalized hydrocarbon macromolecules. In certain embodiments, the macromolecules are Buckminsterfullerenes or Buckyballs. In other embodiments, the Buckyballs are 60 carbon Buckyballs ($C_{60}$) although the invention can also include $C_{70}$ Buckyballs as well as other spherical fullerene molecules and quantum dots.

In certain embodiments, the Buckyballs are functionalized with one or more carboxyl groups. In other embodiments, the Buckyballs are functionalized with three carboxyl groups. In other embodiments, the Buckyballs are $C_{60}$ pyrrolidine tris-acid.

In certain embodiments, the Buckyballs possess an intact carbon cage which retains sufficient hydrophobicity to inhibit adherence to an organic matter matrix and/or a soil matrix.

In certain embodiments, the Buckyballs are functionalized with one or more detectable labels. In other embodiments, the detectable labels are one or more compounds selected from the group consisting of fluorescent tags, radioactive isotopes, amino acids, glycine, tryptophan, arginine and cysteine. In other embodiments, the Buckyballs are functionalized with fluorescent bovine serum albumin (fBSA). In yet other embodiments, the Buckyballs are functionalized with fBSA through a EDC/NHS coupling that activates the carboxylic group, wherein fBSA replaces the NHS ester to form a stable conjugate. In certain embodiments, the Buckyballs are functionalized with $^{14}C$. In certain embodiments, the Buckyballs are functionalized with $^{125}I$.

In certain embodiments, the compositions comprise Buckyballs functionalized with nucleic acids. In other embodiments, the nucleic acids are non-coding RNA oligonucleotides. In other embodiments, the nucleic acids specifically target distinct components of 16S ribosomal RNA. In other embodiments, the Buckyballs can be functionalized with specific RNA oligonucleotide sequences targeting a 16S ribosomal RNA region that is unique to a species of microorganism and specifically identifies that microorganism. In yet other embodiments, the detectable labels are one or more compounds selected from the group consisting of fluorescent tags, radioactive isotopes, amino acids, glycine, tryptophan, arginine and cysteine. In certain embodiments the composition comprises a Buckyball functionalized with a reporter/signature RNA oligonucleotide. In other embodiments, the composition comprises signature information of a certain microbial species. In other embodiments, the composition comprises a Buckyball functionalized with a reporter/signature RNA oligonucleotide and one or more detectable labels.

In certain embodiments, the Buckyball further comprises a protective layer. In other embodiments, the protective layer is a DNA and/or an RNA layer. In other embodiments, the protective layer hybridizes with a nucleic acid which has been functionalized on to the Buckyball. In other embodiments, the protective layer is conjugated with one or more detectable labels. In yet other embodiments, the detectable labels are one or more compounds selected from the group consisting of fluorescent tags, radioactive isotopes, amino acids, glycine, tryptophan, arginine and cysteine. In yet other embodiments, the detectable labels are one or more compounds selected from the group consisting of fBSA, $^{14}C$, $^{125}I$, and cy3/6-FAM In yet other embodiments, the one or more detectable labels conjugated to the protective layer are silent when the protective layer is hybridized to the functionalized Buckyball and active once released.

In certain embodiments, the composition comprises a Buckyball functionalized with a small non-coding RNA. In certain embodiments, the small non-coding RNA is an siRNA. In other embodiments, the small non-coding RNA is one that targets and hybridizes with a specific RNA sequence. In yet other embodiments, the small non-coding RNA is one that targets a specific mRNA. In certain embodiments, the composition further comprises a safeguard RNA which hybridizes to the siRNA to form a complex. In certain embodiments, the functionalized siRNA targets and hybridizes with a specific mRNA sequence, inhibiting its mode of action, silencing certain cellular functions.

In certain embodiments, the composition comprises a Buckyball functionalized with both an rRNA signature sequence as described previously herein and a siRNA sequence as described previously herein. In certain embodiments, the rRNA signature sequence is selected so that the Buckyball recognizes a particular microorganism species, such as a particular bacterium, and the siRNA is selected so that it will hybridize with a specific target mRNA of the particular microorganism, silencing a certain cellular function. In certain embodiments, the composition further comprises a detectable label and a protective layer.

In certain embodiments, the RNA oligonucleotides comprise about 20 to about 50 nucleotides. In other embodiments, the RNA oligonucleotides comprise about 20 to about 30 nucleotides. In other embodiments, the RNA oligonucleotides are conjugated to the Buckyball through an amine group at the 5'. In other embodiments, the RNA oligonucleotides are conjugated to the Buckyball through a covalent bond. In yet other embodiments, the RNA oligonucleotides are conjugated to the Buckyball through an amide bond.

Methods

The invention provides methods of labeling, identifying (e.g. recognizing), differentiating and modifying microorganisms using functionalized Buckyball complexes.

In certain embodiments, the invention provides methods of labeling one or more microorganisms using Buckyballs functionalized with one or more detectable labels, the method comprising contacting the one or more microorganisms with Buckyballs functionalized with one or more detectable labels for a period of time, during which the microorganisms internalize at least a portion of the functionalized Buckyballs. In other embodiments, the one or more detectable labels are one or more compounds selected from the group consisting of fluorescent tags, radioactive isotopes, amino acids, glycine, tryptophan, arginine and cysteine. In yet other embodiments, the one or more detectable labels are selected from the group consisting of fBSA, $^{14}C$ and $^{125}I$. In other embodiments, the Buckyballs are C60-pyrrolidine tris acid.

In certain embodiments, the contacting is a period of incubation. In other embodiments, the contacting/incubating period of time is between 4 minutes and 120 minutes. In other embodiments, the Buckyballs are contacted with the one or more microorganisms in a solution. In yet other embodiments, the Buckyballs contacted in an aqueous solution at a concentration of between about 0.01 µg/mL and about 1000 µg/mL (Buckyballs/solvent).

In certain embodiments, the detectable labels can be detected by one or more methods selected from the group consisting of autoradiography, fluorescence microscopy, X-ray fluorescence microscopy, TEM, and fluorescent spectroscopy In certain embodiments, the invention provides methods of identifying and differentiating live versus dead microorganisms, the method comprising contacting a sample of microorganisms with Buckyballs functionalized with one or more detectable labels for a period of time, measuring the signal from the detectable labels and determining whether a microorganism is alive or dead based on the localized signal emanating from the cell. In other embodiments, the one or more detectable labels are amino acids. In certain embodiments, dead microorganism cells emit higher signals than living cells. Without necessarily subscribing to any single theory, the higher signal in dead cells may be a result of a loss of homeostasis and cell membrane/cell wall integrity, allowing for more rapid internalization of labeled Buckyballs through the cell membrane/cell wall.

In certain embodiments, the invention provides methods of labeling specific species of microorganism within a sample using the RNA functionalized Buckyballs of the invention. The method comprises:
  a) selecting a species of microorganism of interest which has a known genome containing one or more species specific signature RNA sequences;
  b) functionalizing the Buckminsterfullerene molecules with one or more RNA oligonucleotides, wherein the one or more RNA oligonucleotides are complementary to the one or more species specific signature RNA sequences of the microorganism of interest;
  c) hybridizing the one or more RNA oligonucleotides with o protecting layers comprising segments of DNA or RNA and one or more detectable labels; and
  d) incubating a microorganism with the functionalized Buckminsterfullerene molecules for a period of time;
  wherein, the one or more detectable labels are silent when the protecting layer are hybridized to the one or more RNA oligonucleotides and active when the protecting layers are not hybridized; and
  wherein, the functionalized Buckminsterfullerene molecules only label a microorganism in the presence of the one or more species specific signature RNA sequences once internalized into the species of interest and the reporting-protecting layer is released.

In certain embodiments, the invention provides methods of differentiating different species of microorganisms using functionalized Buckyballs of the invention. The method comprises:
  a) synthesizing a species specific detector/reporter Buckyball for each microorganism of interest within a sample, the synthesis comprising;
    i) selecting one or more RNA oligonucleotides which are capable of hybridizing with one or more distinct signature regions of RNA in a microorganism of interest;
    ii) conjugating the one or more RNA oligonucleotides to a functionalized Buckyball;
    iii) hybridizing one or more complementary reporting-protecting layers, which themselves have been conjugated to one or more specific detectable labels, to the one or more RNA oligonucleotides to form a Buckyball-RNA-protecting layer-detectable label complex;
    iv) repeating the synthesis for each microorganism of interest;
  b) contacting a mixture of microorganisms with a mixture of synthesized Buckyballs;
  c) observing and measuring the signal produced within each cell by the one or more specific detectable labels wherein each detectable label corresponds with a different species of microorganism.

In other embodiments, the one or more detectable labels conjugated to the protective layer are silent when the protective layer is hybridized to the functionalized Buckyball and active once released.

In certain embodiments, the RNA oligonucleotides are capable of recognizing and hybridizing with 16S rRNA which is unique to each species of microorganism. In other embodiments, the RNA oligonucleotides are about a 80% to 100% match for the signature RNA region of the organism of interest. In other embodiments, the RNA oligonucleotides comprise about 20 to about 50 nucleotides. In other embodiments, the RNA oligonucleotides comprise about 20 to about 30 nucleotides. In other embodiments, the RNA oligonucleotides are conjugated to the Buckyball through an amine group at the 5'. In other embodiments, the RNA oligonucleotides are conjugated to the Buckyball through a covalent bond. In yet other embodiments, the RNA oligonucleotides are conjugated to the Buckyball through an amide bond. In certain embodiments, the RNA oligonucleotide can be selected through any reasonable means including bioinformatics analysis.

In certain embodiments, the reporting-protecting layer can be a complementary RNA or DNA sequence which is bound to a detectable label. In certain embodiments, the protecting layer is about a 75% match to the RNA oligonucleotide. In certain embodiments, the reporting-protecting layer prevents degradation of the RNA nucleotide. In certain embodiments, the detectable label is silent when the reporting-protecting layer is hybridized with the RNA oligonucleotide but is observable when unbound from the RNA oligonucleotide. In certain embodiments, the reporting-protecting layer is released from the complex when it is replaced by the signature region of RNA in the microorganism of interest.

In certain embodiments, the one or more detectable labels are fluorescent labels, radioactive isotopes, amino acids, nucleic acids, and peptides.

In certain embodiments, the Buckyballs are contacted with the microorganisms in a solution. In other embodiments, the Buckyballs are contacted with the microorganisms in an aqueous solution at a concentration of between about 0.01 µg/mL and about 1000 µg/mL (Buckyballs/solvent).

In certain embodiments, the invention provides methods of inhibiting gene expression in a cell using the RNA functionalized Buckyballs of the invention. The method comprises:
  a) synthesizing functionalized Buckminsterfullerene molecules capable of inhibiting an mRNA segment of interest, the synthesis comprising;
    i) selecting one or more siRNA oligonucleotides which are able to hybridize with the mRNA segment of interest;
    ii) conjugating the one or more siRNA oligonucleotides to a functionalized Buckminsterfullerene molecule;
    iii) hybridizing one or more complementary protecting layers to the one or more siRNA oligonucleotides to form a protected inhibitor complex;
  b) contacting a cell containing the mRNA segment of interest with the synthesized Buckminsterfullerene molecules; and
c) allowing the microorganisms to internalize the Buckminsterfullerene molecules, whereby the functionalized siRNA oligonucleotides can hybridize with free mRNA in the cytoplasm, preventing transcription and gene expression.

In certain embodiments, the invention provides methods of detecting and imaging gene expression in a cell using the RNA functionalized Buckyballs of the invention. The method comprises:

a) synthesizing functionalized Buckminsterfullerene molecules capable of binding an mRNA segment of interest corresponding to the gene of interest, the synthesis comprising;

i) selecting one or more siRNA oligonucleotides which are able to hybridize with the mRNA segment of interest;
   ii) conjugating the one or more siRNA oligonucleotides to a functionalized Buckminsterfullerene molecule;
   iii) hybridizing one or more complementary protecting layers to the one or more siRNA oligonucleotides to form a protected inhibitor complex, wherein the one or more complementary protecting layers are conjugated with a detectable label which is silent when the protecting layer is hybridized and active when it is not hybridized;
b) contacting a cell containing the mRNA segment of interest with the synthesized Buckminsterfullerene molecules; and
c) allowing the microorganisms to internalize the Buckminsterfullerene molecules, whereby the functionalized siRNA oligonucleotides can hybridize with free mRNA in the cytoplasm, releasing the complementary protecting layer.

In certain embodiments, the siRNA oligonucleotides are capable of recognizing and hybridizing with mRNA which is unique to a specific species of microorganism. In other embodiments, the RNA oligonucleotides are about a 80% to a 100% match for the mRNA segment of interest. In other embodiments, the siRNA oligonucleotides comprise about 20 to about 50 nucleotides. In other embodiments, the siRNA oligonucleotides comprise about 20 to about 30 nucleotides. In other embodiments, the siRNA oligonucleotides are conjugated to the Buckyball through an amine group at the 5'. In other embodiments, the siRNA oligonucleotides are conjugated to the Buckyball through a covalent bond. In yet other embodiments, the siRNA oligonucleotides are conjugated to the Buckyball through an amide bond. In certain embodiments, the siRNA oligonucleotide can be selected through any reasonable means including bioinformatics analysis.

The invention further provides a combined method of simultaneously differentiating different species of microorganism and inhibiting gene expression in a specific microorganism using the RNA functionalized Buckyballs of the invention. The method comprises:

a) synthesizing species specific reporter/inhibitor Buckyballs for each microorganism of interest within a sample, the synthesis comprising;
   i) selecting one or more RNA oligonucleotides which are capable of hybridizing with one or more distinct signature regions of RNA in a microorganism of interest;
   ii) selecting one or more siRNA oligonucleotides which are capable of hybridizing with one or more distinct mRNA segments of interest;
   iii) conjugating the one or more RNA oligonucleotides and siRNA oligonucleotides to a functionalized Buckyball;
   iv) hybridizing one or more complementary reporting-protecting layers for the RNA oligonucleotides, which themselves have been conjugated to one or more specific detectable labels, to the one or more RNA oligonucleotides and hybridizing one or more complementary protecting layers to the one or more siRNA oligonucleotides to form a Buckyball-RNA/siRNA-protecting layer-detectable label complex;
   v) repeating the synthesis for each microorganism of interest;
b) contacting a mixture of microorganisms with a mixture of synthesized Buckyballs;

c) visualizing and measuring the signal produced within each cell by the one or more specific detectable labels wherein each detectable label corresponds with a different species of microorganism.

In certain embodiments, each Buckyball can be functionalized with RNA corresponding to multiple different microorganisms. In other embodiments, a single batch of Buckyballs may be synthesized which have been functionalized with RNA oligonucleotides corresponding to two or more different microorganisms and reporting-protecting layers, each conjugated with different detectable labels wherein once the Buckyballs have been internalized, they will only release the appropriate reporting-protecting layer such that the identity of the microorganism can be determined by observing and measuring the signal from the detectable label.

In certain embodiments, the method does not require sample fixation. In other embodiments, the methods can be used with living microorganisms. In yet other embodiments, the methods can be used to visual, monitor and profile mRNA expression by dynamic visualization.

In certain embodiments, the functionalized Buckyballs are synthesized with substituents that eliminate stickiness (adherence) to an organic matrix or the microbial environment.

Devices and Systems

The invention further provides devices and systems for differentiating microorganisms within a microbial community using the compositions and methods of the invention.

In certain embodiments, the invention comprises a system comprising one or more source wells and one or more sink wells wherein the one or more source wells are in fluidic communication with the one or more sink wells. Each of the one or more sink wells independently comprises one or more Buckyball compositions of the invention functionalized to recognize a specific species of microorganism and release a specific detectable label in the presence of said microorganism and optionally a microbial attractant specifically chosen to attract said microorganism. By selectively releasing a specific detectable label which corresponds to a specific species, this allows the system to determine the presence or absence of a species of microorganism in a well. In certain embodiments, the one or more Buckyball compositions are printed into the one or more sink wells.

In certain embodiments of the system, a microbial sample mixture comprising one or more microorganism species is placed in the source well. The microbial sample mixture will then disperse, spreading the microorganisms to the sink wells through random diffusion, propulsion or through active locomotion by the microorganisms. In certain embodiments, certain microorganisms will be attracted to specific wells due to the presence of a microbial attractant. In certain embodiments, a microorganism that has entered a sink well will internalize one or more of the Buckyballs of the invention. In other embodiments, if the microorganism internalizes a Buckyball comprising an RNA oligonucleotide corresponding to a matching sequence in the microorganism, the Buckyball will release a reporting-protecting layer comprising a detectable label, producing a detectable signal. In certain embodiments, the signal emitted by the detectable label can be measured to determine the presence or absence of the corresponding microorganism as well as the relative abundance of said microorganism.

In certain embodiments, the microbial attractant is a nutrient, mineral or environmental condition which would selectively draw a microorganism of interest to sink well. In certain embodiments, the microbial attractant can be one or more conditions selected from the group consisting of a sugar gradient, a protein gradient, a metal ion gradient, a temperature gradient, a salinity gradient, a light gradient and a specific wavelength of light.

In certain embodiments, each sink well comprises a different Buckyball composition of the invention capable of detecting a different species of microorganism. In certain embodiments, one or more sink wells comprise Buckyball compositions capable of detecting multiple species of microorganisms.

In certain embodiments, the system comprises about 2 to about 1,000 sink wells. In other embodiments, the system comprises a number of sink wells equivalent to the number of identified microbial species present in a studied microbial system. For example, the typical human oral cavity comprises a microbial biome which is home to hundreds of well characterized species. In certain embodiments, a system designed to study 100 highly prevalent microorganisms native to the human oral cavity can have about 100 sink wells, each sink well comprising a Buckyball functionalized with an RNA oligonucleotide specifically designed to hybridize with a signature RNA sequence unique to one of the microbial species present in a typical human oral cavity, and each Buckyball further comprising a unique detectable label conjugated to a reporting-protecting layer.

In certain embodiments, the system further comprises one or more control wells. In other embodiments, the control wells do not comprise compositions of the invention. In other embodiments, the control wells comprise unfunctionalized Buckyballs. In yet other embodiments, a portion of the control wells are positive controls wherein the wells comprise microorganisms of a known population density which have been exposed to the corresponding Buckyballs of the invention and emit a signal from the detectable label which can be used as a basis of comparison.

In certain embodiments, the system further comprises one or more imaging devices capable of rapidly recording a signal from the one or more sink wells to determine the presence or absence of signaling microorganisms in each well as well as the relative signal intensities. In other embodiments, the imaging device can report this information to a user as an estimated microbial density for each species within the sample mixture.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

Although the description herein contains many embodiments, these should not be construed as limiting the scope of the invention but as merely providing illustrations of some of the presently preferred embodiments of the invention.

All references throughout this application (for example, patent documents including issued or granted patents or equivalents; patent application publications; and non-patent literature documents or other source material) are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application. In general the terms and phrases used herein have their art-recognized meaning, which can be found by reference to standard texts, journal references and contexts known to those skilled in the art. Any preceding definitions are provided to clarify their specific use in the context of the invention.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.
Materials and Methods
Conjugation of Fluorescent Bovine Serum Albumin/Amino Acids C60-pyrrolidine tris acid (1 mg) (Sigma) was dispersed in 0.5 mL of 2-(N-morpholino)ethanosulfonic acid (pH 5.6) (MES) (Sigma) buffer under sonication for 30 min at ambient conditions. 0.25 mL of 1-(3-dimethylaminopropyl)-3-ethylcarbodiimide hydrochloride (0.4 mol/L) (EDC) (Sigma) and 0.25 ml of N-hydroxysuccinimide (0.2 mol/L) (NHS) (Sigma) in MES solution were added to the activated carboxylate groups. The mixture was washed with PBS and centrifuged at 12,000 g for 30 min in a 5 KDa molecular weight cutoff centrifugal filter (Millipore) for 5 times, to remove EDC and NHS. 2 mg of fluorescent bovine serum albumin (fBSA) (Sigma)/cysteine (Acros) were then added into the C60-pyrrolidine tris acid/PBS solution at 4° C. overnight for conjugation. The mixture was finally washed with PBS and centrifuged in a micro-centrifuge tube to remove un-conjugated protein/cysteine in supernatant; this centrifugation was repeated 5 times at 12,000 rcf for 30 min. The C60-pyrrolidine tris acid-fBSA/cysteine pellet was collected and stored at −20° C. until use.

For further labeling C60-pyrrolidine tris-cysteine with Atto565 NHS Easter (Sigma), C60-pyrrolidine tris-cysteine (1 mg) were suspended in 1 mL EDC/MES solution (0.1 mol/L); Atto 565 NHS Easter (20 μL) was then added at 4° C. overnight for conjugation. The mixture was finally washed with PBS and centrifuged in a micro-centrifuge tube to remove un-conjugated Atto565 in supernatant; the centrifugation was repeated 5 times at 12,000 rcf for 30 min. The C60-pyrrolidine tris acid-cysteine-Atto565 pellet was collected and stored at −20° C. until use.
Radio-Labeling of $^{14}C$ and $^{125}I$ to C60-Pyrrolidine Tris Acid $^{14}C$ labeling was carried out on dry ice and under argon in the fume hood. C60-pyrrolidine tris acid (100 μg) was dispersed in 1 mL dimethylformamide (DMF) (Sigma) homogeneously in a 15 mL conical tube. Potassium carbonate (1 mg) was added as base. Then, 50 μL $^{14}C$-methyl iodide (1.85 MBq) was added, and the tube was capped tightly. Until this point, $H_2O$ was avoided. The tube was transferred at room temperature to allow the mixture to react for 1 hour with periodic agitation (every 10 min). Potassium carbonate was then removed while excess DMF and unreacted $^{14}C$-methyl iodide were evaporated using an oil bath. Next, $^{14}C$ labeled C60-pyrrolidine tris acid was suspended in 1 mL DMF, and its radioactivity was counted in the liquid scintillation counter. The radiochemical yield was calculated as ~20% as following:

$$\text{Radiochemical Yield} = \frac{\text{Product Radioactivity}}{\text{Added Radioactivity}} \times 100\% \qquad \text{Equation 1}$$

$^{125}I$-labeling was performed under ambient conditions in a 1.5 mL microcentrifuge tube. C60-pyrrolidine tris acid (100 μg) was dispersed in 1 mL phosphate buffer (pH 8.0). 5 μL of $Na^{125}I$ (0.56 MBq) and 5 μL of N-chlorosuccinimide (10 mg/mL in DI $H_2O$) were then added. The reaction was allowed to continue for 20 min with periodic shaking (every 5 min). The reaction was then quenched by adding 10 μL of sodium bisulphite (10 mg/mL in DI $H_2O$) (Sigma) and 10 μL of NaI (10 mg/mL in DI $H_2O$) (Sigma). The mixture was centrifuged at 20,000 rcf for 15 min to pellet the $^{125}I$-labeled C60-pyrrolidine tris acid. The pellet was washed with DI $H_2O$ and re-pelleted 5 times at 20,000 rcf for 15 min until the radioactivity of the wash reached normal level. The yield was calculated to be ~20% according by Equation 1.
Fluorescence Microscopy A Zeiss 710 confocal microscopy system fluorescence microscope was utilized to (i) profile microbial and matrix autofluorescence, and microbial uptake, (ii) differentiate live and dead cells, and (iii) evaluate adherence to the matrix. Depending upon the use-case, samples were imaged with either a Zeiss Plan-Neofluar 10×/0.30 objective or a Plan-Apochromat 63×/1.40 Oil immersion objective. The soil matrices were imaged with the 10× objective, while microbial species were imaged and subsequently quantified with the 63× objective. The excitation filters were set at 488 and 561 nm, and the emission filters were set to receive signals between 493-556 nm and 597-700 nm, respectively. The laser intensity was set at 20% to excite fBSA and matrix autofluorescence. A twin-gate main beam splitter with two wheels and each wheel having 10 filter positions (e.g., 100 possible combinations) was used to separate excitation and emission beams. The pinhole was set at 600 μm to receive as many photons as possible.

To examine the auto-fluorescence of microorganisms, 1.0 mL of bacterial cells ($OD_{630}$=0.6) were pelleted by centrifugation at 5,000 rcf to remove the old medium, then suspended in 1.0 mL fresh medium. 5 μL of the suspension was then mounted onto a glass slide under a coverslip, sealed with nail polish hardener. To examine the retention of C60-pyrrolidine tris acid within the microorganisms, 1.0 mL of bacterial cells ($OD_{630}$=0.6) were pelleted at 5,000 rcf to remove the old medium. Cells were suspended in fresh medium in a 1.5 mL micro-centrifuge tube and incubated in the dark at with C60-pyrrolidine tris acid-fBSA (5 µg/mL) predetermined times: 5 min, 30 min, 1 hour, and 2 hours. The tube was then centrifuged at 5,000 rcf to remove the non-penetrated C60-pyrrolidine tris acid-fBSA, and the microorganisms were suspended in fresh medium. 5 µL of the suspension was then mounted onto a glass slide under a coverslip, sealed with nail polish hardener.

To examine the retention of C60-pyrrolidine tris acid within the microorganisms after wash, the pellets were washed with DI $H_2O$, and the C60-pyrrolidine tris acid-fBSA internalized microorganisms were re-pelleted at 5,000 rcf for 5 min in the dark. This was repeated 6 times. 5 µL of the suspension was then mounted onto a glass slide under a coverslip, sealed with nail polish hardener. The fluorescent images were taken using a Zeiss 710 confocal microscopy system.

To differentiate live and dead microorganisms, freshly prepared C60-pyrrolidine tris-cysteine-Atto565 conjugate was used. First, live or dead microorganisms (*E. coli* and *B. subtilis*) (dead cells were obtained by incubating live cells at 90° C. for 30 minutes) were incubated in the dark with C60-cysteine-Atto565 (10 µg/mL) for 30 min. Second, both live and dead microorganisms were pelleted at 5,000 rcf for 5 min, and the supernatant was carefully removed. Third, the live and dead microorganism pellets were washed with DI $H_2O$, then re-pelleted. Finally, 5 µL of the final suspensions for live and dead microorganism were mounted onto two respective glass slides under coverslips, sealed with nail polish hardener. The prepared slides were imaged using a Zeiss 710 confocal microscope under identical microscopic conditions (e.g., laser intensity, pinhole setting, gain). The images obtained with the Zeiss 710 confocal microscope were not modified by other software and were analyzed by ImageJ software. The process of the image analysis is: (I) The fluorescent signal of the microorganisms (single cell or cluster of cells) were selected by the freehand selection tool and the background signal was subtracted. (II) The mean intensity of the selected area was measured by ImageJ. (III) The average signal was then calculated by averaging the mean intensity of multiple selected areas.

To examine the adherence of C60-pyrrolidine tris acid to the matrix, several substrates were used. These are VWR Sand (VWR), alumina (Acros), glass beads, wild sand (collected at the Aquatic Park Innovation Center, Berkeley Calif.), and natural soil (collected at the backyard garden of Aquatic Park Innovation Center, Berkeley Calif., courtesy of the building management). These substrates (0.2 g) were incubated in the dark with 1 mL C60-pyrrolidine tris acid-fBSA (5 µg/mL) for 30 min. Each substrate was then washed 6 times with 1 mL DI $H_2O$ (10 min incubation). Next, 10 grains of substrate particle were carefully dried of liquid, and then mounted onto glass slides with nail polish hardener as a sealant. The fluorescent images were taken by Zeiss 710 confocal microscope.

Retention of C60-Derivatives from Multiple Substrates

To examine the retention of C60-derivatives in multiple substrates with different masses (2 g, 4 g, 6 g, and 8 g), each substrate (e.g., wild sand, natural soil, VWR sand) was incubated with C60-pyrrolidine tris acid at a concentration of 5 µg/mL on a layer of filter paper (with an average pore size of 25 µm). After 30 min of incubation, vacuum suction was applied, and the first filter-through of C60-pyrrolidine tris acid was collected. The residue on the filter paper was washed with DI $H_2O$ (10 min of incubation), and the filter-through of C60-pyrrolidine tris acid was collected for the second time. Both filter-throughs were measured by UV-vis spectrometer at 335 nm. The recovery of C60-pyrrolidine tris acid was determined as following:

$$\text{Recovery of } C60-\text{Pyrrolidine Tris Acid} = \frac{\text{Absorption of Filter-throughs at 335 nm}}{\text{Original amount of } C60 \text{ at 335 nm}} \times 100\% \quad \text{Equation 2}$$

Transmission Electron Microscopy (TEM)

TEM was used to examine whether the retention of C60-pyrrolidine tris acid was localized within the cytosol. Microorganisms were incubated with C60-pyrrolidine tris acid (5 µg/mL) for 30 min. Cells were pelleted by centrifugation at 5,000 rcf (5 min) and washed 5 times with DI $H_2O$. Microorganisms were fixed in 2.5% glutaraldehyde/PBS solution for 30 min. The cells were then pelleted by centrifugation at 5,000 rcf for 5 min. The cell pellet was placed in fresh 2.5% glutaraldehyde/PBS solution at 4° C. overnight. Next, cell pellets were dehydrated by a series of acetone treatments (30% for 15 min, 50% for 15 min, 70% for 15 min, 90% for 15 min and a final treatment at 100% for 30 min, and repeated 3 times), embedded in resin (2:1 mix of propylene oxide:resin for 1 hour, 1:1 mix of propylene oxide:resin for 1 hour, 1:2 mix of propylene oxide:resin for 1 hour, 100% resin overnight, and change to fresh resin 1 h), incubated for 24 h at 37° C., sectioned (60 nm in thickness), and imaged using a Tecnai 12 TEM.

Liquid Scintillation Counter

To examine the retention of C60-pyrrolidine tris acid within multiple substrates, each substrate (0.2 g) was incubated in the dark with 1 mL of $^{14}C$ labeled C60-pyrrolidine tris acid (5 µg/mL) for 30 min. The substrate was pelleted without microorganisms at 5,000 rcf and washed those pellets 6 times with 1 mL DI $H_2O$ (10 min incubation). The final pellets were added to 3 mL of scintillation cocktail. The data were recorded using a liquid scintillation counter (Perkin Elmer).

Autoradiography

To examine the retention of C60-pyrrolidine tris acid in *B. subtilis* and *E. coli* with multiple substrates, each substrate (0.2 g) was incubated in the dark with 1 mL $^{14}C$- and $^{125}I$-labeled C60-pyrrolidine tris acid (5 µg/mL) for 30 min. Substrates both with and without microorganisms were pelleted at 5,000 rcf and washed those pellets 5 times with 1 mL fresh DI $H_2O$ (10 min incubation). The final pellet was dispersed in 0.1 mL fresh LB broth. 1/10 of the volume was carefully transferred onto a piece of plastic wrap, under which was a phosphor imager film. After 24 hours of sitting in complete darkness, the film was transferred into a Cyclone Plus Phosphor Imager (Perkin Elmer) for imaging.

Cell Culture

*E. coli* (Invitrogen) and *B. subtilis* (ATCC) were cultured in LB Broth at 37° C. with constant shaking. *E. coli* and *B. subtilis* were not used until $OD_{630}$ reached 0.6.

Statistical Analysis

Four samples were analyzed at each condition. The data in the graphs are represented by their mean±standard deviation (SD).

Preparation of Microfluidics

Glass slides (Fisher Scientific) were washed with ethanol, dried with air, and exposed to 4 mW/cm² UV light (UVP, LLC) for 2 hr. The hyrogel precursor (0.5 mL) consists of 10% (v/v) 700 MW PEG diacrylate (PEG-DA) (Sigma) and 0.5% (v/v) 2-hydroxy-2-methylpropiophenone (Sigma), and is evenly distributed over the glass slides by a spin coater (SCK-200P). The slides were then placed under approximately 4 mW/cm² UV light for 15 seconds under a mask to gel. The slides were then incubated in 50 mM triethylene glycol mono-mercaptoundecyl ether (Sigma) for 15 min, rinsed in 70% ethanol for 15 min and washed with DI water. During this process, the microfluidics is stored in humid environment to avoid desiccation.

Example 1: Synthesis of Functionalized C60-Pyrrolidine Tris Acid

C60-pyrrolidine tris acid is a derivative of fullerene C60 (FIG. 1) and possesses three key properties: (i) containing three carboxyl groups that allow for further decoration (e.g., fluorescent tagging and radioactive isotope labeling); (ii) being extremely small (1-2 nm for a single molecule, 10-20 nm for a cluster of molecules), which facilitates intercellular movement and actions; and (iii) maintaining an intact carbon cage that retains enough hydrophobicity to inhibit adherence of C60-pyrrolidine tris acid to the soil matrix and organic matter. C60 was evaluated as both a fluorescent and radiotracer reporter, where the rationale for functionalization is summarized below.

(i) Functionalization of C60-pyrrolidine tris acid with fBSA is based on EDC/NHS coupling that activates the carboxylic group, where fBSA replaces the NHS ester to form a stable conjugate.

(ii) Functionalization of C60-pyrrolidine tris acid with $^{14}C$ was based on the methylation of the carboxyl group with potassium hydroxide/dimethyl sulfate and radioactive methyl iodide. The final yield of $^{14}C$-methylated C60-pyrrolidine tris acid was about 20%.

(iii) Functionalization of C60-pyrrolidine tris acid with $^{125}I$ uses the Finkelstein reaction. First, C60-pyrrolidine tris acid was functionalized with Cl by using N-chlorosuccinimide. Second, Cl was replaced by $^{125}I$ through the Finkelstein reaction. The final yield of $^{125}I$-labeled C60-pyrrolidine tris acid was about 20%.

Example 2: Microbial Internalization of C60-Pyrrolidine Tris Acid

In order to visualize whether C60-pyrrolidine tris acid can internalize within microorganisms, a three-step validation protocol was used that involved fluorescence microscopy, transmission electron microscopy (TEM), and autoradiography. The model organisms included both Gram-negative and Gram-positive bacteria.

E. coli (Gram-negative) and B. subtilis (Gram-positive) were incubated with functionalized C60-pyrrolidine tris acid with fBSA for 30 minutes. Samples were then washed with DI H₂O to remove excess probes, and samples were then imaged by confocal microscopy. FIG. 2 indicates a positive association of C60-pyrrolidine tris acid with microorganisms, where in FIGS. 2A and 2B, both E. coli and B. subtilis have fluorescent signal emission following excitation by a 488 nm laser. It was confirmed that these fluorescent signals are solely from C60-pyrrolidine tris acid-fBSA, because neither E. coli nor B. subtilis has an auto-fluorescence signal under the same conditions in the absence of fluorescent C60 (FIGS. 12A-12F). In addition, these fluorescent signals co-localize with E. coli and B. subtilis cells by combining bright field and fluorescent imaging, which indicates either internalization within the cell or binding to the cell wall.

Figure 3A:
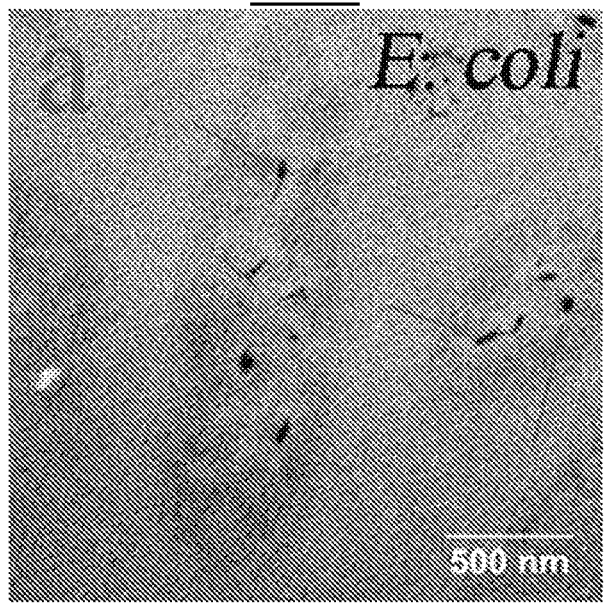
FIGS. 3A and 3B illustrate cellular uptake of C60-pyrrolidine tris acid by *E. coli* and *B. subtilis* monitored by Transmission Electron Microscopy. The dark spots, pointed by the arrows, represent C60-pyrrolidine-tris acid uptake by *E. coli* (FIG. 3A) and *B. subtilis* (FIG. 3B).
Figure 3B:
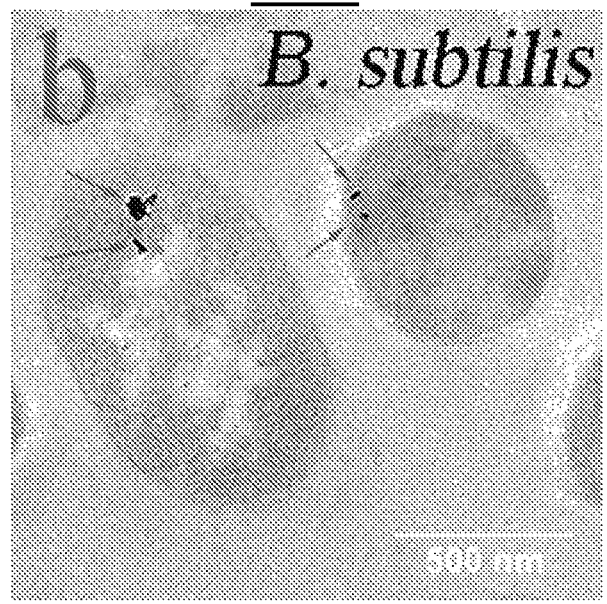
Figure 4A:
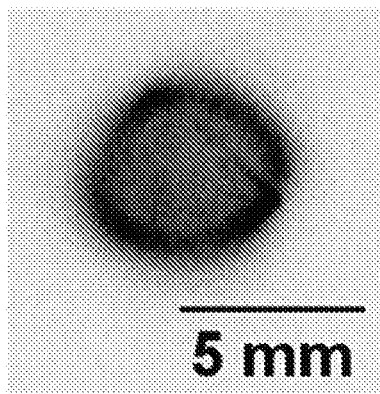
FIGS. 4A-4D illustrate cellular uptake of radiotracers labelled C60-pyrrolidine tris acid by microorganisms monitored by Autoradiography.
Figure 4B:
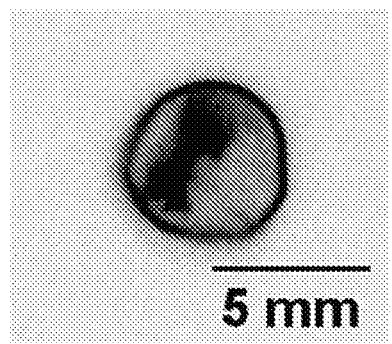
Figure 4C:
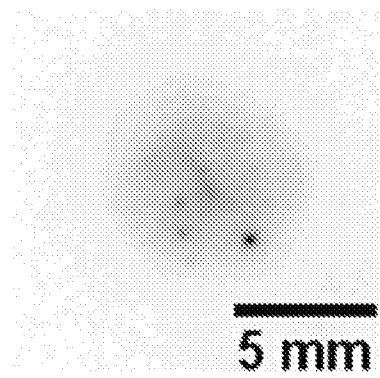
Figure 4D:
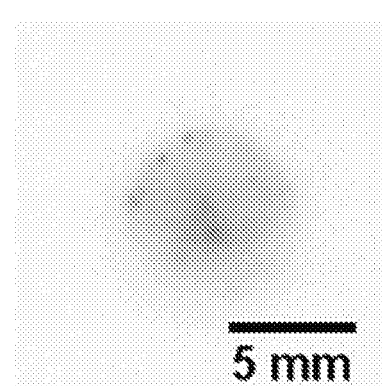

To test the hypothesis that functionalized C60-pyrrolidine tris acid internalizes within the cell, microorganisms were imaged with TEM. Both E. coli and B. subtilis were incubated with C60-pyrrolidine tris acid, washed to remove excess compound, sectioned into slices of 60 nm thickness, and then imaged by TEM. FIGS. 3A and 3B shows that C60-pyrrolidine tris acid localizes within the cell in both E. coli and B. subtilis, respectively. The control study consisted of (i) C60-pyrrolidine tris acid in DI H₂O, (ii) C60-pyrrolidine tris acid on a mouse tissue section, (iii) an E. coli section without C60-pyrrolidine tris acid incubation, and (iv) a B. subtilis section without C60-pyrrolidine tris acid incubation. These data are shown in FIGS. 13A-13D. These results indicate positive cellular uptake of C60-derivatives in microorganisms, hence providing an opportunity to monitor the cellular activity in situ by further functionalization of C60.

Figure 14:
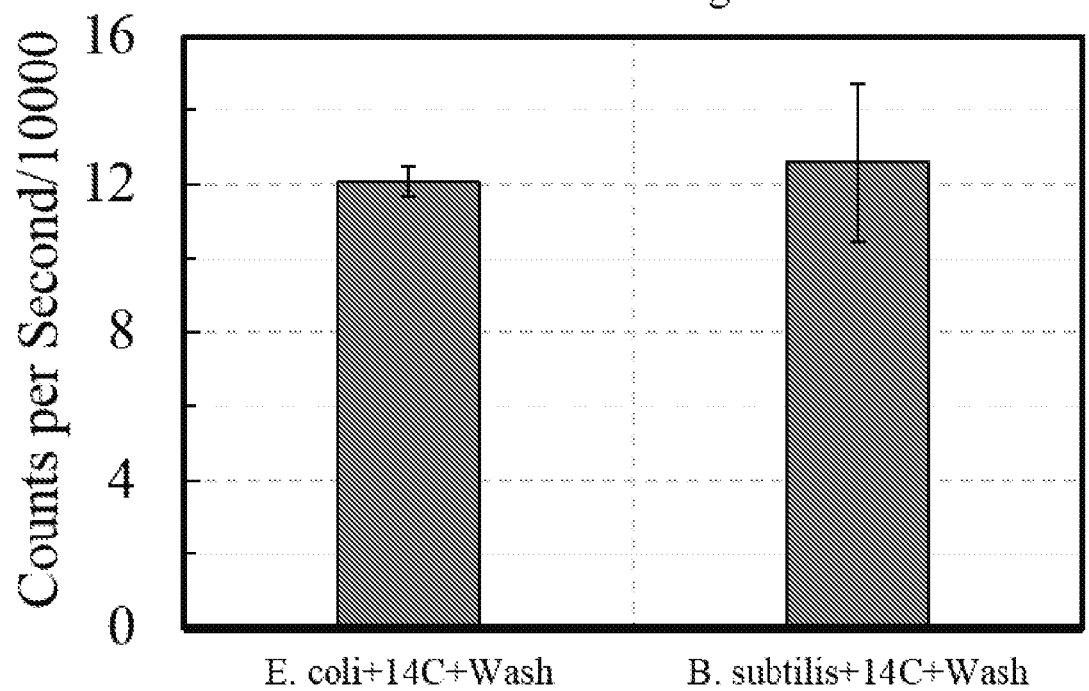
FIG. 14 illustrates uptake of $^{14}$C-labelled C60-pyrrolidine tris acid monitored by Liquid Scintillation Count for *E. coli* and *B. subtilis*.

It was next determined whether C60-pyrrolidine tris acid could be radiolabeled, which would thus provide a platform for imaging thick sections in an opaque environment. C60-pyrrolidine tris acid was functionalized with $^{14}C$ and $^{125}I$, and samples are incubated as before. FIGS. 4A-4D shows β-radiation and γ-radiation emission from both E. coli (FIGS. 4A and 4C) and B. subtilis (FIGS. 4B and 4D), which are incubated with $^{14}C$- and $^{125}I$-labeled C60-pyrrolidine tris acid and imaged through autoradiography. The liquid scintillation data (FIG. 14) also shows a positive association of $^{14}C$-methylated C60-pyrrolidine tris acid by both E. coli and B. subtilis (about 12,000 counts per second). These results provide additional confirmation that C60-pyrrolidine tris acid can be internalized by microbes and visualized.

Finally, to investigate whether the number of washes or the incubation time has an impact on the C60 internalization, these parameters are changed, and the previous studies were repeated. The rationale was that internalization might be a function of combined physical size, electrostatics, hydrophobicity, and diffusivity. Results, shown in FIGS. 15A-H and FIGS. 16A and 16B and Tables 1 and 2, indicate that cellular (i) uptake is correlated with increased incubation time, and (ii) retention is not affected by the number of washes. These results were obtained through unbiased and automated quantitative analysis, with an example shown in FIG. 17.

TABLE 1

Quantified signal intensity for FIGS. 15A-15H

| | Microorganism Signal Intensity | Background Signal Intensity |
|---|---|---|
| FIG. 15A | 273 ± 71 | 40 ± 8 |
| FIG. 15B | 345 ± 56 | 120 ± 10 |
| FIG. 15C | 372 ± 103 | 70 ± 15 |
| FIG. 15D | 529 ± 105 | 150 ± 13 |
| FIG. 15E | 654 ± 54 | 224 ± 48 |
| FIG. 15F | 860 ± 123 | 257 ± 32 |
| FIG. 15G | 1128 ± 210 | 321 ± 22 |
| FIG. 15H | 1323 ± 239 | 284 ± 41 |

TABLE 2

Signal intensity for FIGS. 16A and 16B

| | Microorganism Signal Intensity | Background Signal Intensity |
|---|---|---|
| FIG. 16A | 579 ± 167 | 40 ± 15 |
| FIG. 16B | 942 ± 167 | 225 ± 34 |

Example 3: Non-Stickiness of C60-Pyrrolidine Tris Acid to the Substrates

Chemical staining dyes and antibodies for immunostaining known in the art are usually sticky to the natural environment (e.g., soil, sand), creating significant background noise during visualization. Therefore, the non-stickiness of the C60-derivatives of the invention were determined. The degree of non-stickiness was evaluated using a variety of substrates (e.g., glass beads, alumina, VWR sand, wild sand, and natural soil), with UV absorption and imaging that includes both fluorescence microscopy and use of an autoradiography/scintillation counter. These substrates covered a range of synthetic and natural environments for validation, while the readouts provided both bulk (e.g., UV absorption) and spatial information (e.g., imaging). The results are summarized below.

Figure 18:
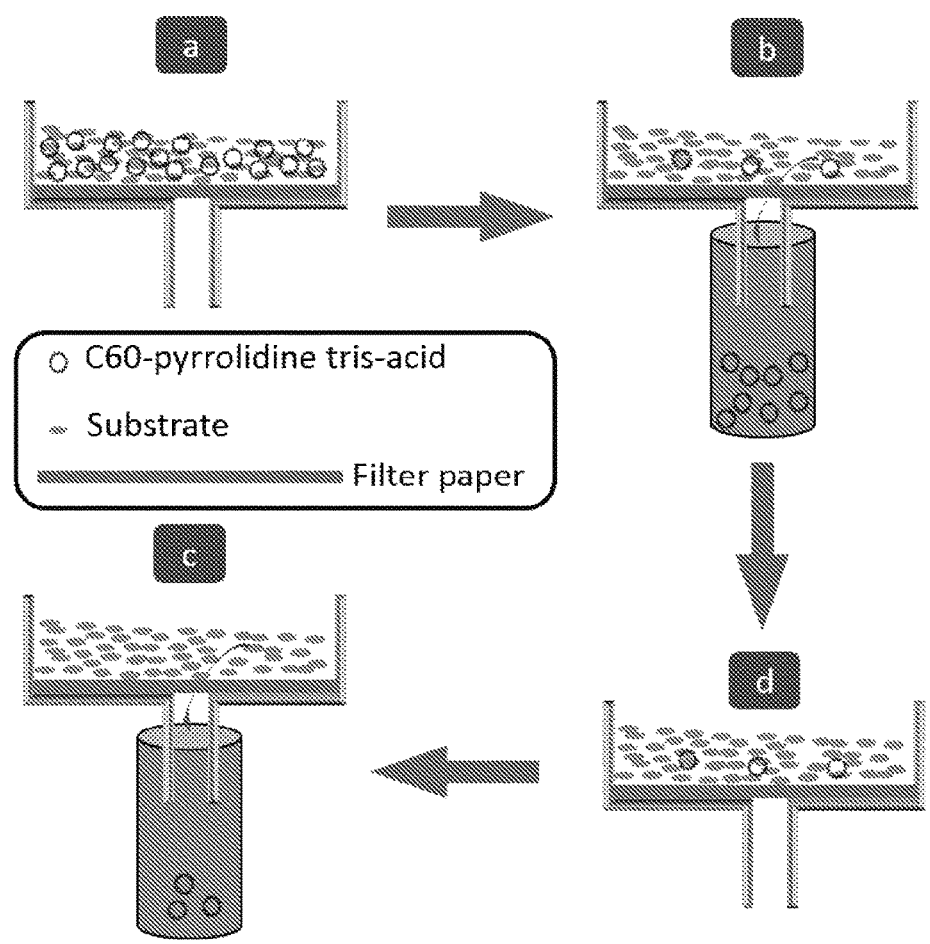
FIG. 18 provide experimental setup for measuring UV absorption: (a) Incubate C60-pyrrolidine tris acid with the substrate for 30 mins, (b) apply a vacuum manifold to C60-pyrrolidine tris acid and collect filtrate, (c) add fresh water to the substrate again and incubate for another 30 mins, and (d) apply a vacuum manifold to wash water and collect filtrate again.

The non-stickiness of the C60 derivatives was determined by incubating functionalized C60-pyrrolidine tris acid solution in a substrate on a layer of filter paper, applying a vacuum to remove the solution, and running one or more $H_2O$ washes through the substrate (FIG. 18). The stickiness of C60-pyrrolidine tris acid was quantified with multiple substrates, by measuring the UV absorption of filter-through at 335 nm, which is the specific absorption wavelength of C60. FIG. 5A indicates that more than 70% of the C60-pyrrolidine tris acid was recovered from silica without $H_2O$ wash (red column) regardless of the mass of matrix. With respect to non-synthetic substrates, similar recovery rates were reported for homogenized VWR sand (>80%, FIG. 5B), Wild Sand (>60%, FIG. 5C), and Natural Soil (>70%, FIG. 5D), all without $H_2O$ wash (red column). The remainder of C60-pyrrolidine tris acid is fully recovered from the matrices, following $H_2O$ rinses (green columns in FIGS. 5A-5D). These results indicate that C60-pyrrolidine tris acid is not sticky to the natural environment. The rationale for requiring a second wash is due to the meso-porous architecture of the matrices that trap C60-derivatives.

Figure 6A:
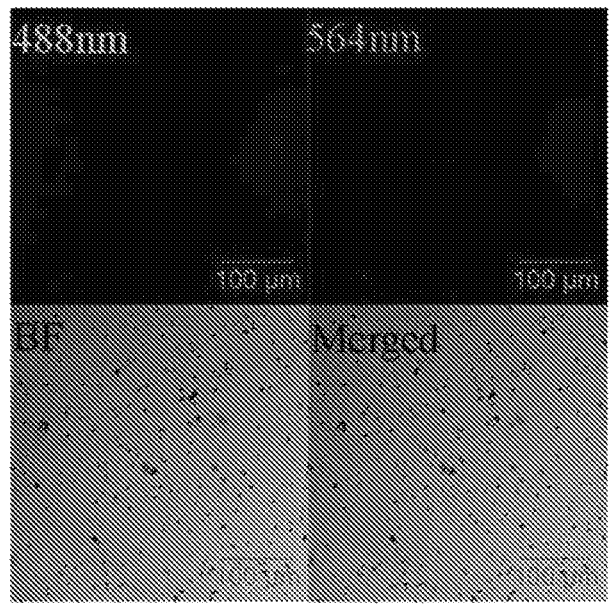
FIGS. 6A and 6B illustrate the non-stickiness of C60-pyrrolidine tris acid monitored by Confocal Laser Scanning Microscopy following several washes. Fluorescence microscopy indicates that C60-pyrrolidine tris acid had no adherence to alumina (FIG. 6A) and glass beads (FIG. 6B), which are clearly present in bright field microscopy.
Figure 6B:
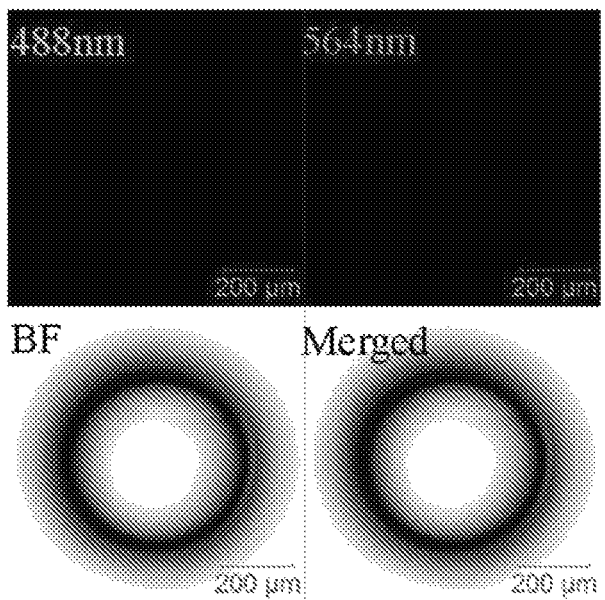
Figure 19C:
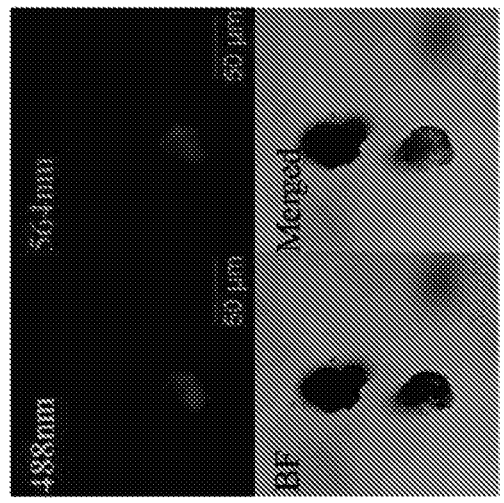
FIGS. 19A-19C illustrate auto-fluorescence of (FIG. 19A) VWR sand, (FIG. 19B) wild sand, and (FIG. 19C) natural soil, all monitored by confocal microscopy with 488 nm excitation.
Figure 19B:
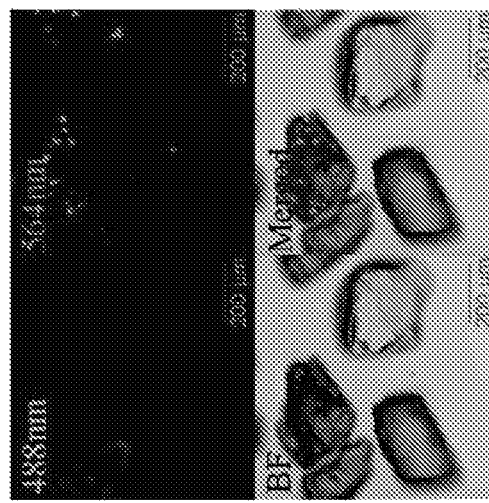
Figure 19A:
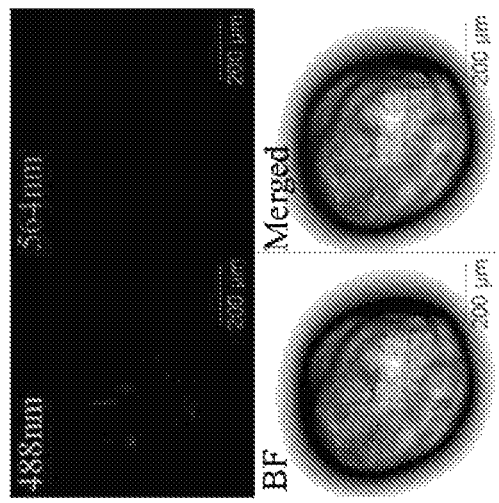

To investigate the non-stickiness of C60-pyrrolidine tris acid spatially, several studies were designed. (I) fBSA-labeled C60-pyrrolidine tris acid was evaluated against non-auto-fluorescent matrices such as glass beads and alumina (FIGS. 6A and 6B). Using fluorescence microscopy, each substrate emits an initial fluorescent signal after incubation with C60-pyrrolidine tris-fBSA, with the signal being lost following multiple $H_2O$ washes, thus providing confirmation that C60-pyrrolidine was not sticky to the natural environment. (II) fBSA-labeled C60-pyrrolidine tris acid was evaluated against matrices such as VWR sand, wild sand, and natural soil (FIG. 19). However, these matrices are auto-fluorescent and mask fluorescent probes, making it difficult to visualize the fluorescent-labeled C60. (Ill) Further validation by autoradiography and liquid scintillation is pursued in all substrates (e.g., pretreated VWR sand, glass beads, alumina, wild sand, and natural soil). FIG. 7 indicates that neither β- nor γ-radiation were detected from incubated matrices (middle and right columns) after $6H_2O$ rinses. Therefore, the disclosed C60-derivatives are non-sticky to the natural environment and can be removed entirely by $H_2O$ washes.

Figure 8:
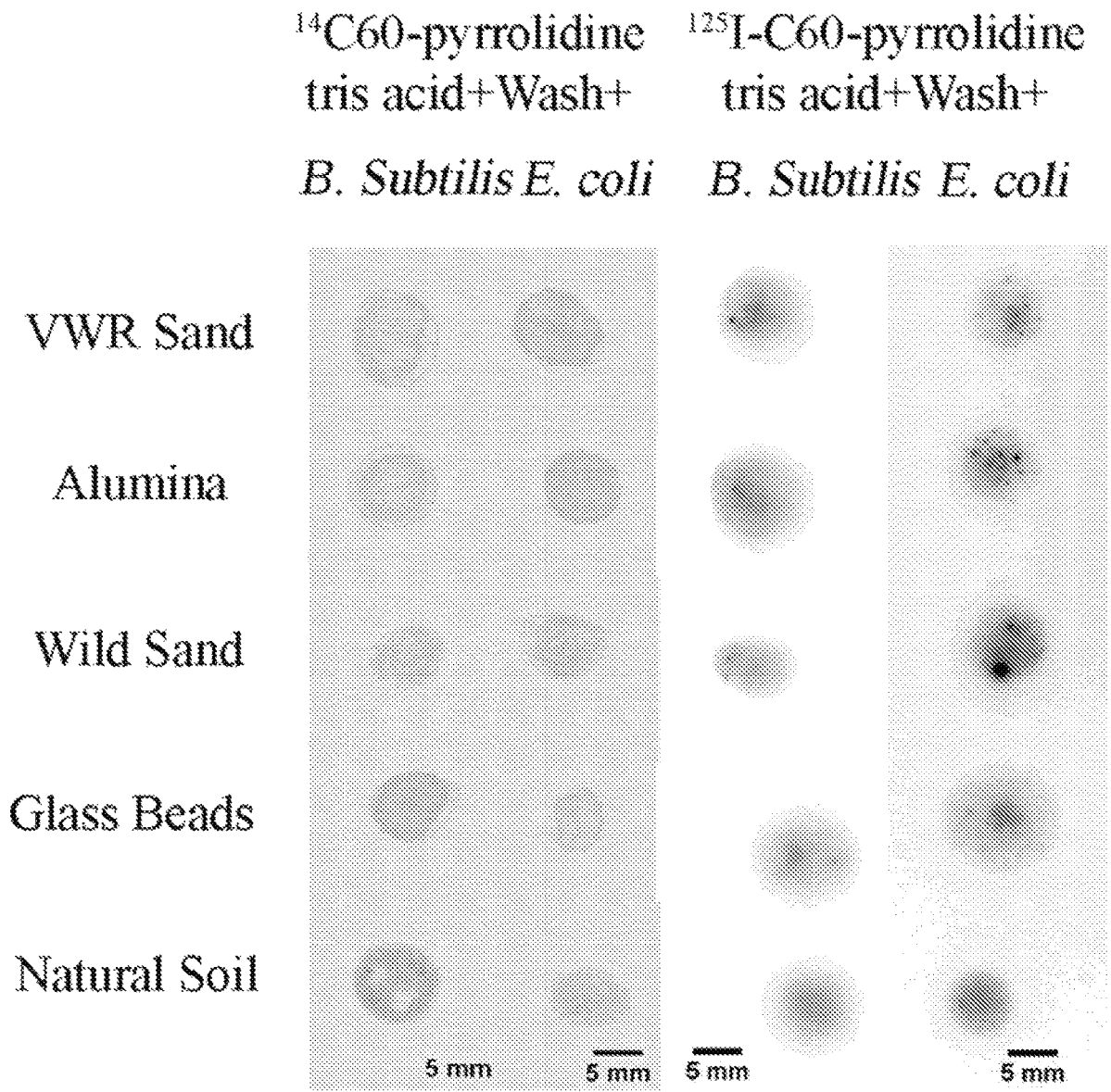
FIG. 8 illustrates cellular uptake of microorganisms embedded in different matrices and monitored by autoradiography following several washes. Left and right columns indicate uptake by $^{14}$C- and $^{125}$I-labelled C60-pyrrolidine tris acid on *B. subtilis* and *E. coli*, respectively. The data indicate a residual signal that is presumably due to the uptake of microorganisms, since FIG. 7 indicates non-stickiness to the same substrates.
Figure 9:
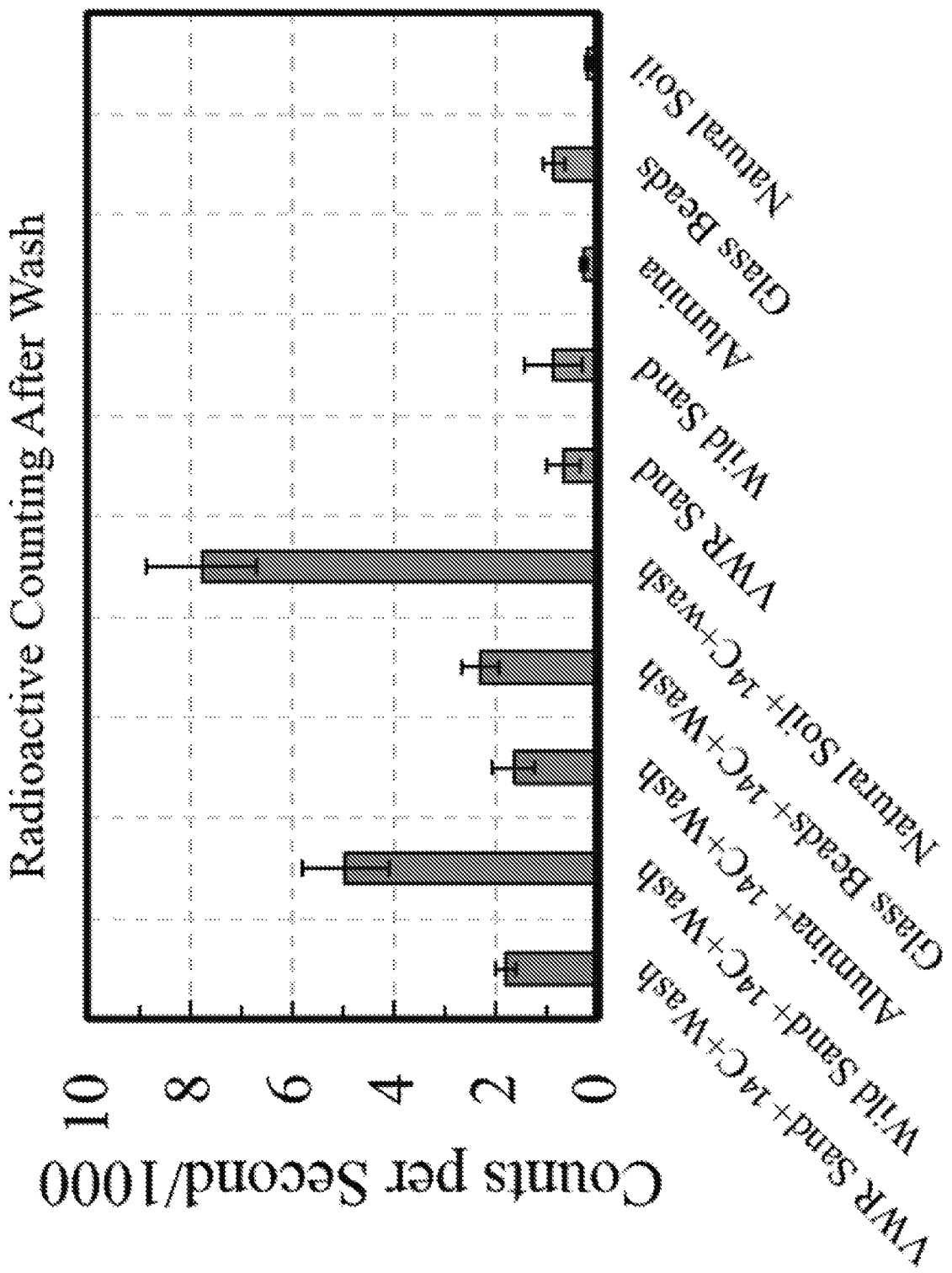
FIG. 9 illustrates the non-stickiness of $^{14}$C-labelled C60-pyrrolidine tris acid with five different matrices, monitored by Liquid Scintillation Count (LSC) following several washes. Hatched columns show similar level of LSC from incubation and washout of VWR sand, wild sand, alumina, glass beads, and natural soil with $^{14}$C labelled-C60-pyrrolidine tris acid. Filled bars show the background LSC on the same substrates.

Example 4: Uptake of Functionalized C60-Pyrrolidine Tris Acid in Microbes Embedded in Soil Matrices Natural soil is a complicated biomaterial, hosting thousands of microorganisms with intrinsic organic and inorganic matters that hinder probe delivery. $^{14}C$- and $^{125}I$-radiolabeled C60-pyrrolidine tris acid are incubated with a mixture of soil and microorganisms and then washed to remove excess probes as before. The autoradiography, shown in FIG. 8, indicates strong β- and γ-radiation from the mixture of soil and microorganisms. Comparison of this result with both (i) FIGS. 4A and 4B, which indicated association with microorganisms, and (ii) FIGS. 7A and 7B, which indicated non-stickiness to the matrix, suggests that radiotracers can label microbes in their native environment. Moreover, interesting observations are made when 3-radiation is quantified using a liquid scintillation counter, comparing both control and treated matrices with $^{14}C$-labeled C60-pyrrolidine tris acid. All control matrices (e.g., background) show around 1,000 counts per second (FIG. 9, filled columns), while $^{14}C$-labeled C60-pyrrolidine tris acid incubated with glass beads, alumina, VWR sand, wild sand, and natural soil show 2,000, 2,000, 2,000, 4,000, and 6,000 counts per second respectively (FIG. 9, hatched columns). These results indicate that the natural microorganisms in wild sand and natural soil have successfully taken up $^{14}C$-labeled C60-pyrrolidine tris acid, which accounts for the increased number of counts per second.

Example 5: Differentiation of Live and Dead Microorganisms

To investigate differentiation between live and dead cells, C60 was functionalized with four different amino acids and then screened. This approach was motivated by the fact that different microorganisms have varying preferences for a specific amino acid. C60-pyrrolidine tris acid was functionalized with the amino acids glycine, tryptophan, arginine, and cysteine. In particular, cysteine functionalized C60-pyrrolidine tris acid allowed for the differentiation of live and dead cells in the presence of the substrate matrix.

To validate non-stickiness to the matrix, both UV absorption and microscopy are utilized. FIGS. 10A-10D show a trend for recovering C60-pyrrolidine tris-cysteine from alumina (FIG. 10A), VWR sand (FIG. 10B), wild sand (FIG. 10C), and natural soil (FIG. 10D), all of which show results comparable to those previously reported (FIG. 5). More than 60% of C60-pyrrolidine tris-cysteine is removed from alumina, wild sand, and natural soil, without wash (hatched column). The rest of C60-pyrrolidine tris-cysteine was fully recovered with one additional $H_2O$ wash (filled column).

Figure 11:
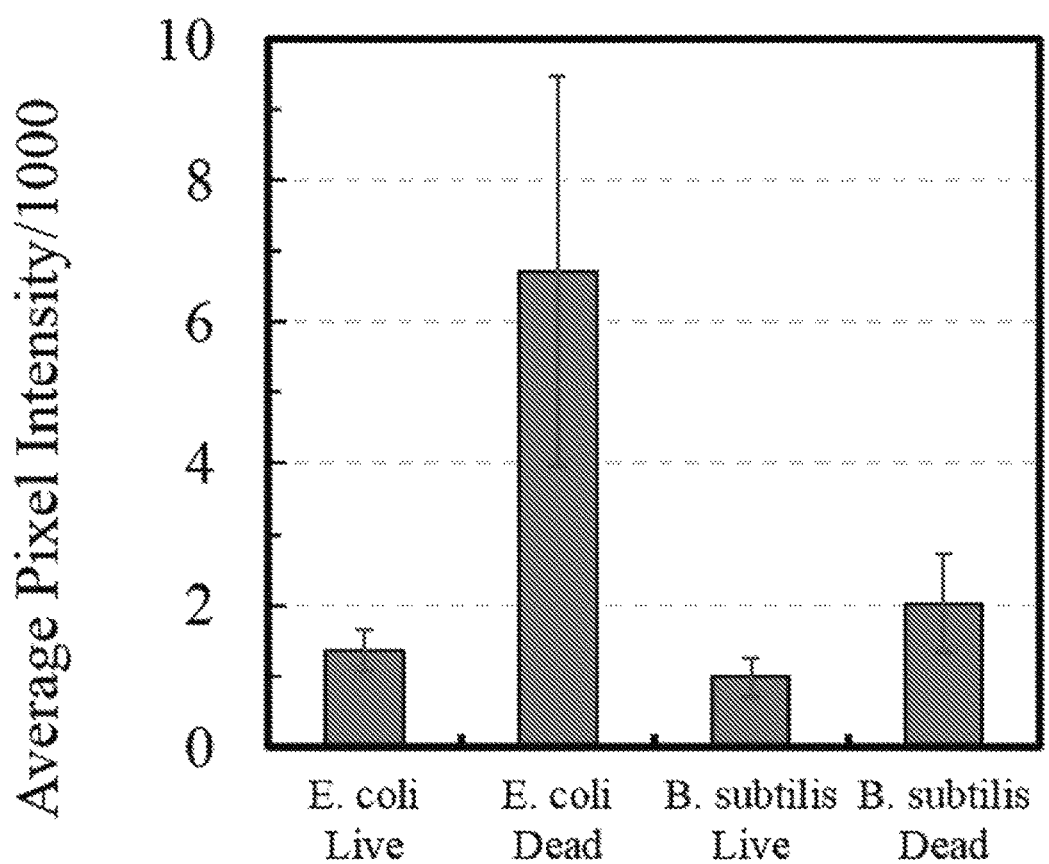
FIG. 11 indicates cellular uptake C60-Cystine for differentiating live and dead microorganisms (*E. coli* and *B. subtilis*), quantified by analyzing images from confocal microscopy. Live microorganisms showed a significantly lower uptake than the dead microorganisms. The uptake was quantified by the average pixel intensities of microorganisms over the background.
Figure 12A:
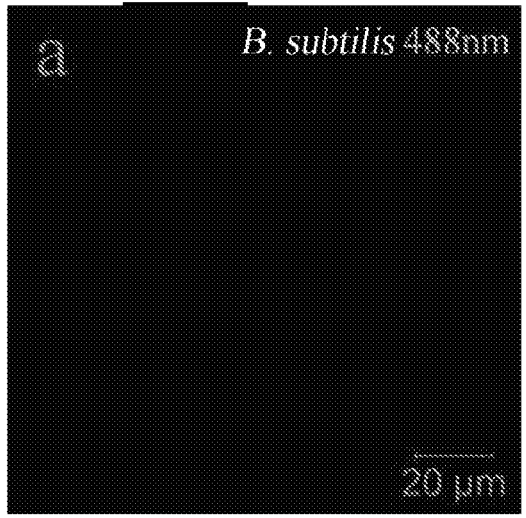
FIGS. 12A-12F illustrate autofluorescence of *B. subtilis* and *E. coli* monitored with a confocal microscope indicate no signals.
Figure 12B:
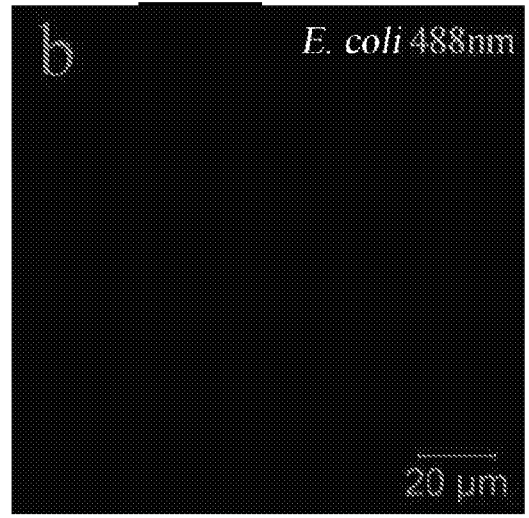
Figure 12C:
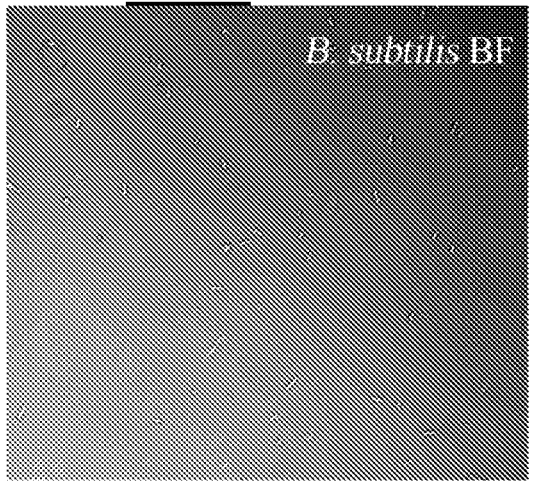
Figure 12D:
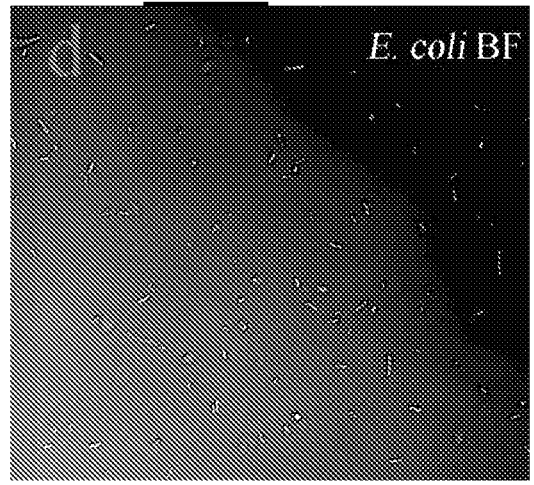
Figure 12E:
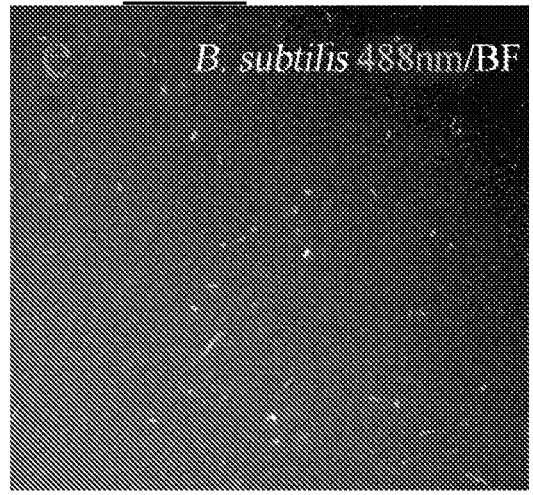
Figure 12F:
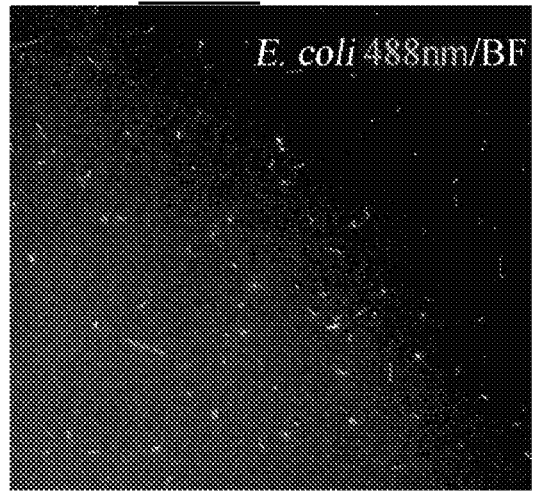
Figure 13A:
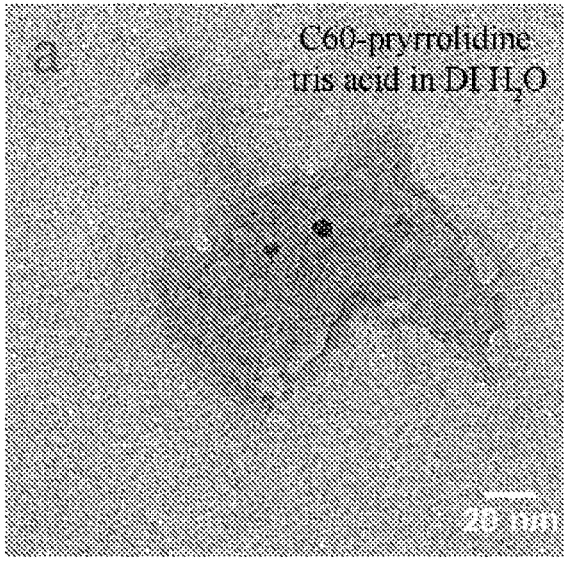
FIGS. 13A-13D illustrate positive and negative controls for C60-pyrrolidine tris acid monitored with transmission electron microcopy. C60-pyrrolidine tris acid is clearly present in (FIG. 13A) DI $H_2O$ and (FIG. 13B) a tissue section from mouse as background. The background, without C60-pyrrolidine tris acid, is void of any signal in (FIG. 13C) *E. Coli* and (FIG. 13D) *B. subtilis*.
Figure 13B:
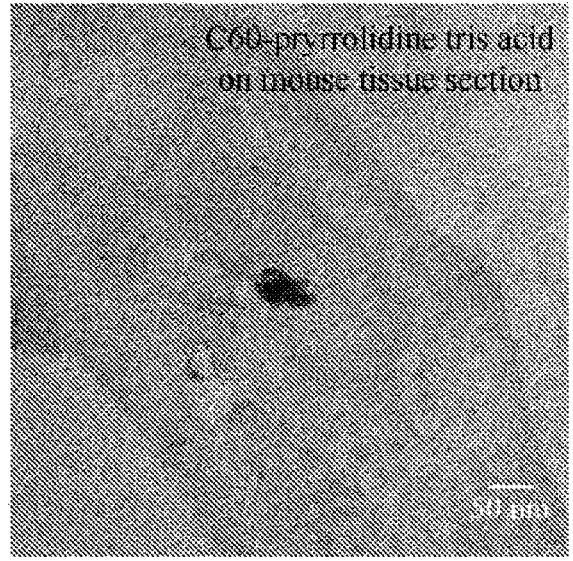
Figure 13C:
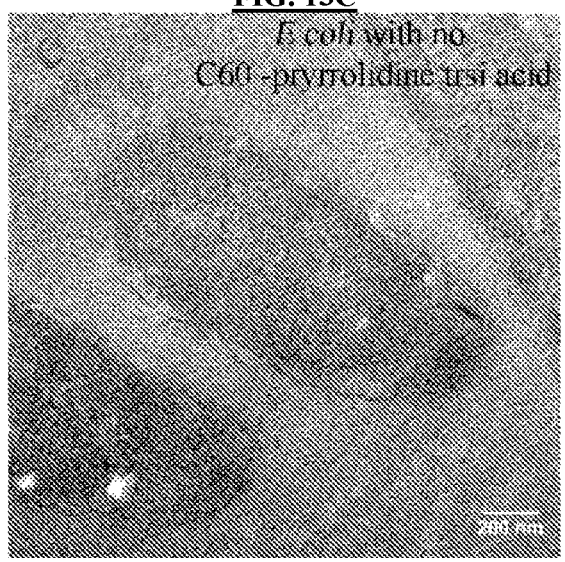
Figure 13D:
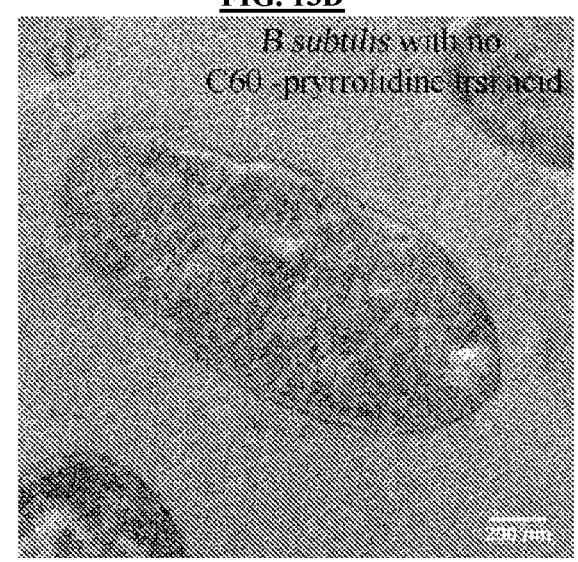

To differentiate and quantify live and dead microorganisms, fluorescence microscopy was used. The results indicate a significantly lower signal for live cells than for dead cells for both *E. coli* and *B. subtilis*, as shown in FIG. 11. Both live *E. coli* and *B. subtilis* showed a base line fluorescence signal of approximately 1,000 (in pixel intensity), whereas dead *E. coli* and *B. subtilis* showed a significantly higher signals, of approximately 6,500 and 2,000, respectively. This observation is potentially due to the fact the dead cells have a leaky structure, which allows more C60-pyrrolidine tris-cysteine to cross their cellular membrane. In addition, the cell wall of dead *B. subtilis* (Gram-positive, and with a thicker cell wall) may not be as leaky as dead *E. coli*; thus, dead *E. coli* shows a higher fluorescence signal than *B. subtilis*. The net result is that functionalized C60-pyrrolidine tris acid can differentiate cellular states.

Figure 20A:
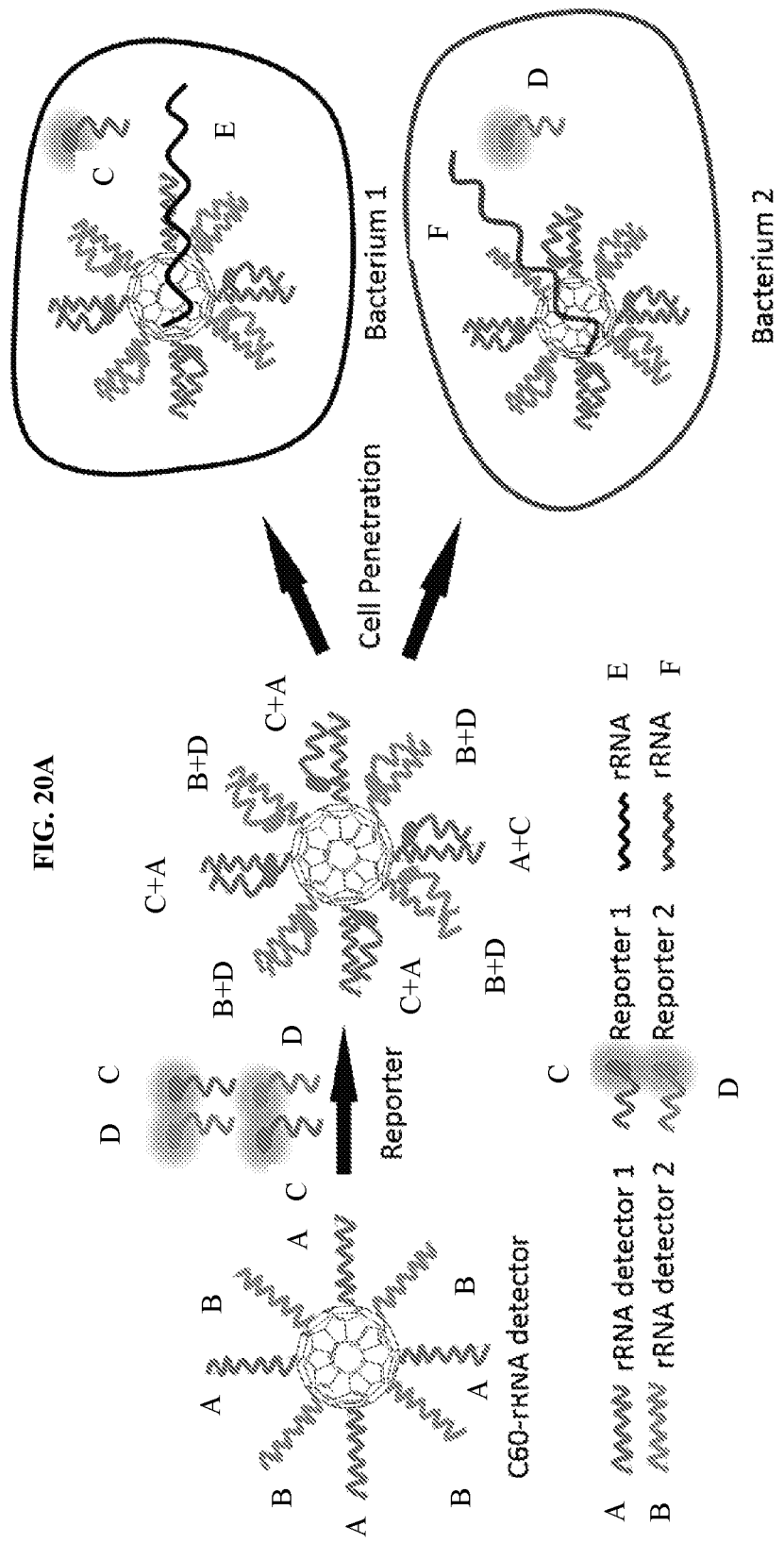
Figure 20B:
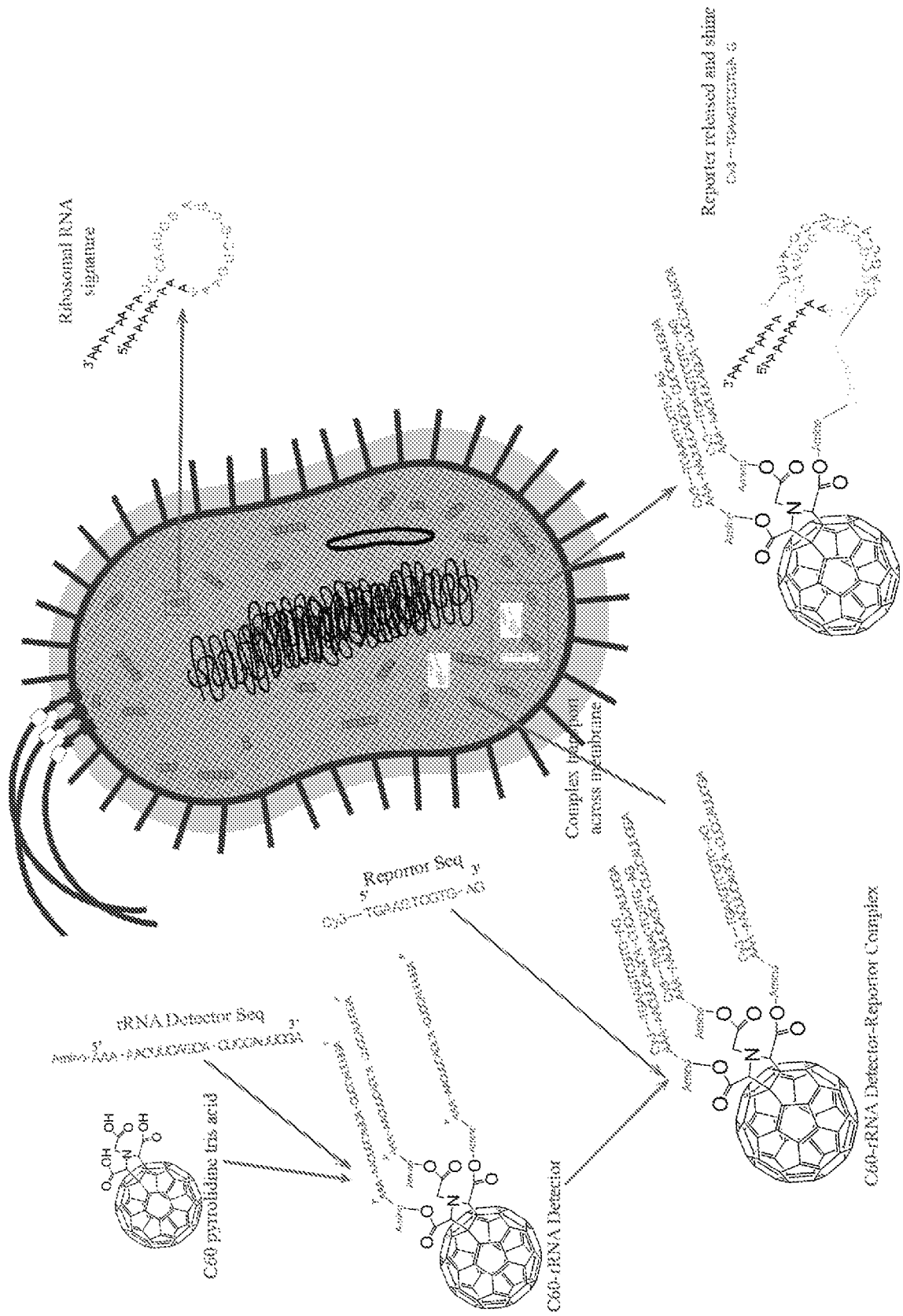

Example 6: Methods of Distinguishing Live Bacteria with C60 Functionalized with Reporter RNA Oligo Methods were developed to distinguish different species of live bacteria by functionalization of C60 with RNA oligonucleotides hybridized with reporter compounds. The signature RNA oligonucleotides are designed in accordance with the signature information on 16s ribosome RNA, which is unique to each species (Reischl et al., *Clin Chem* 52, 1985-1987 (2006) and Dresios et al., *Journal of molecular biology* 345, 681-693 (2005), each of which is hereby incorporated by reference in its entirety). The strategy to recognize a certain bacteria is shown in FIGS. 20A-20C and operates as follows:

(1) C60 molecules were functionalized with signature RNA oligonucleotides containing signature information (e.g., calling card) of a certain species. The Signature RNA oligonucleotides were typically screened through bioinformatics analysis.

(2) A reporter sequence, which is conjugated to a fluorophore, was hybridized with the signature sequence. The fluorophore was silent while hybridized but fluoresced once released.

(3) The C60 complex penetrated the bacteria and released the reporter if the bacteria contained ribosomal signature information that matches the signature RNA oligonucleotide on the C60 complex. The released reporter sequence emitted a fluorescent signal and was detected while free in the cytoplasm.

Figure 21:
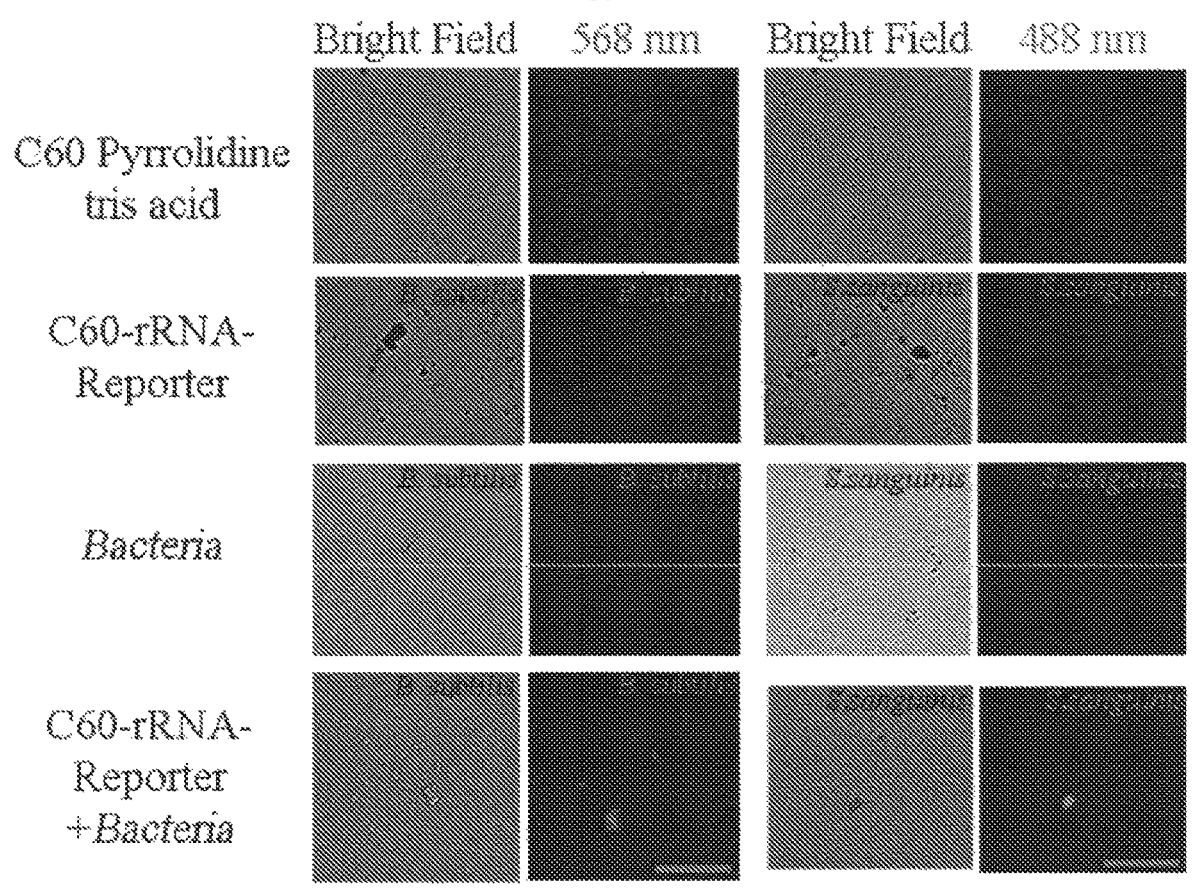
FIG. 21 is a series of images illustrating the differentiation of *B. subtilis* and *S. sanguinis* by disclosed C60-rRNA-Reporter complex. Scale bar is 10 μm.

To validate the protocol, functionalized C60s, with a distinct region of rRNA, were synthesized for live imaging *B. subtilis* and *S. sanguinis*, which are gram-positive/negative, respectively. The 16s RNA signature sequence was reported by Gendel, et al (Gendel, Food Microbiol 13, 1-15 (1996)), which is hereby incorporated by reference in its entirety, with an amine group at the 5' end. A 75% matching reporter with a cy3/6-FAM fluorophore at 5' was hybridized with the signature RNA. The whole C60 complex (10 µg/mL) was incubated with *B. subtilis* for 30 minutes. The results are shown in FIGS. 21 and 22 and are summarized as follows:

(1) C60 pyrrolidine tris acid, *B. subtilis* and *S. sanguinis* have no autofluorescence under the excitation of 568 nm laser.

(2) The C60-rRNA-Reporter has no fluorescent signal under excitation with a 488 or 568 nm laser, indicating that the fluorophore is silenced by hybridization.

(3) The C60-rRNA-Reporter can distinguish *B. subtilis* or *S. sanguinis* by fluorescent signal when the reporter has been released by hybridizing with matching ribosomal RNA.

(4) Each C60-rRNA-Reporter complex is only capable of recognizing a single bacterial species with a signature rRNA sequence.

(5) A mixture of C60-rRNA-Reporters can further distinguish a mixture of *B. subtilis* and *S. sanguinis* in live status.

Example 7: C60-siRNA Complexes Used for Silencing Gene Expression mRNA conveys genetic information that is transcribed from DNA. This genetic information can be translated into proteins, thus carrying out specific cellular functions. In eukaryotic cells, precursor mRNA is transcribed and post edited in the nucleus, where C60 molecules cannot reach. However, mature mRNA is transferred into the cell cytoplasm as an template for translation. In this state, mRNA can be targeted by the C60-rRNA complexes of the invention.

Figure 23:
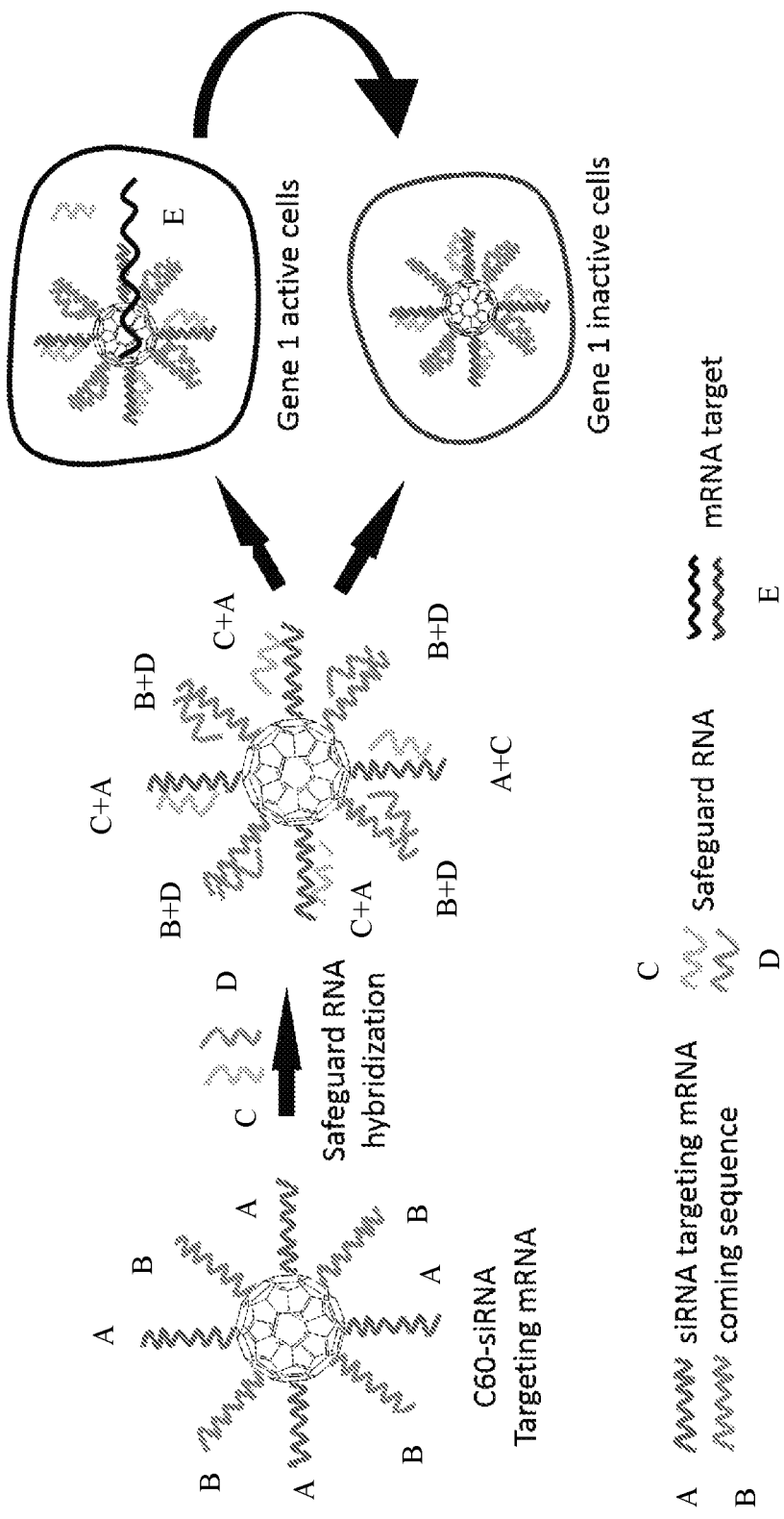
FIG. 23 is a schematic illustrating a method for generating C60-siRNA complexes that can be used for regulating gene expression.

A schematic of this process is provided in FIG. 23 and operates as follows:

(1) C60 pyrrolidine-tris acid is functionalized with siRNA, the sequence of which is selected based on the desired target genes.

(2) A protecting RNA hybridizes the attached siRNA, preventing degradation. Optionally, the protecting RNA can be functionalized with a detectable label which is silent while the protecting RNA is hybridized but detectable if it is released.

(3) The C60-siRNA complex is transported across the cellular membrane. Once inside:

(i) If the target gene is active and the corresponding mRNA is present in the cytoplasm, the attached siRNA releases the protecting RNA, targets the active mRNA and shuts down the translation by competitively hybridizing with it. If a detectable label is bound to the protecting RNA, the label will begin emitting.

(ii) If the target gene is inactive, the siRNA would remain hybridized to the protecting RNA.

The compositions of the invention can therefore be used to silence multiple genes by using a specifically designed probe to light up cells in which certain cell functions are shut down and/or be designed to activate/stimulate certain cell functions.

Figure 24:
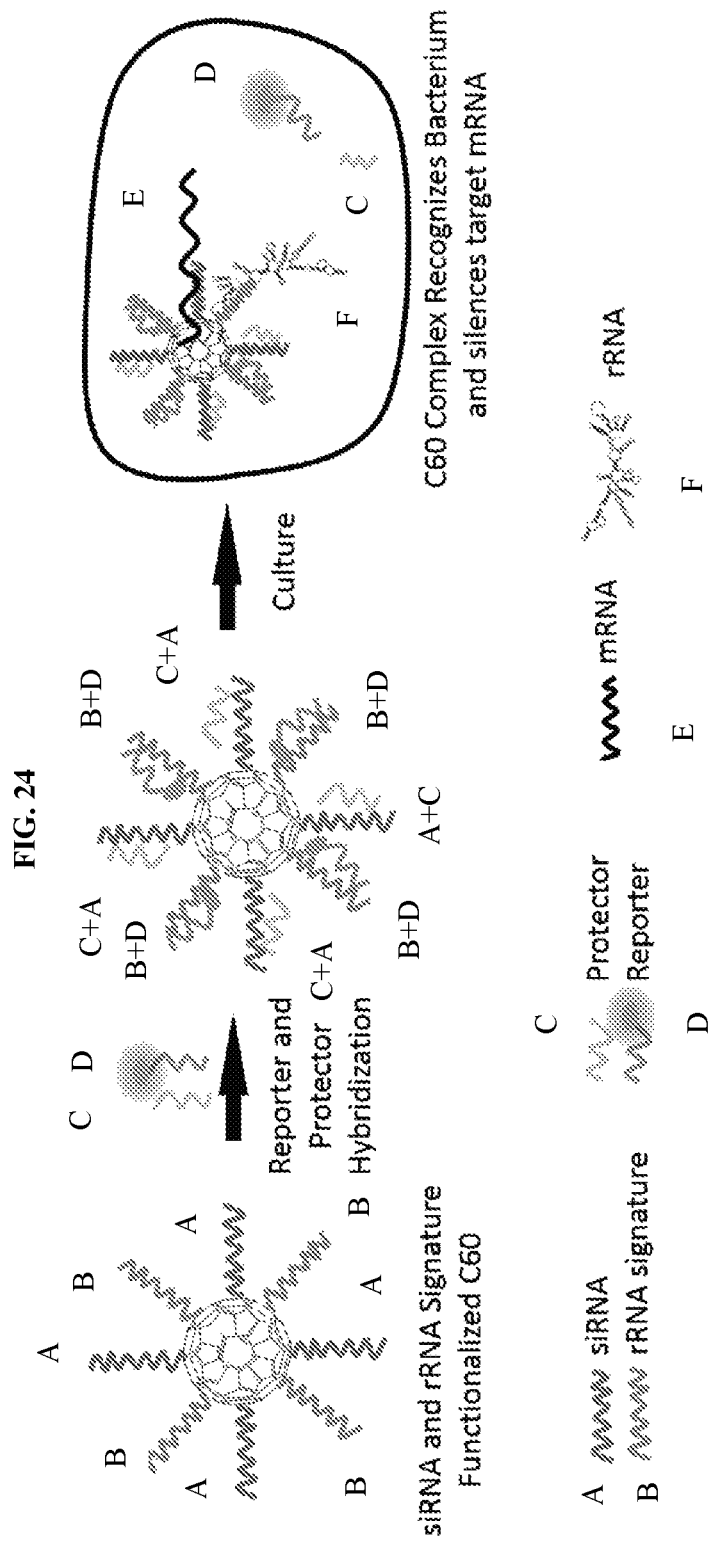
FIG. 24 is a schematic illustrating a method for simultaneously imaging a specific bacterium and activating or suppressing transcription in the specific bacterium.

In certain embodiments, a Buckyball can be functionalized to detect 16s RNA as described in Example 6 and simultaneously inhibit mRNA transcription as described above in Example 7 in a single step. An illustration of this embodiment is shown in FIG. 24.

Figure 25:
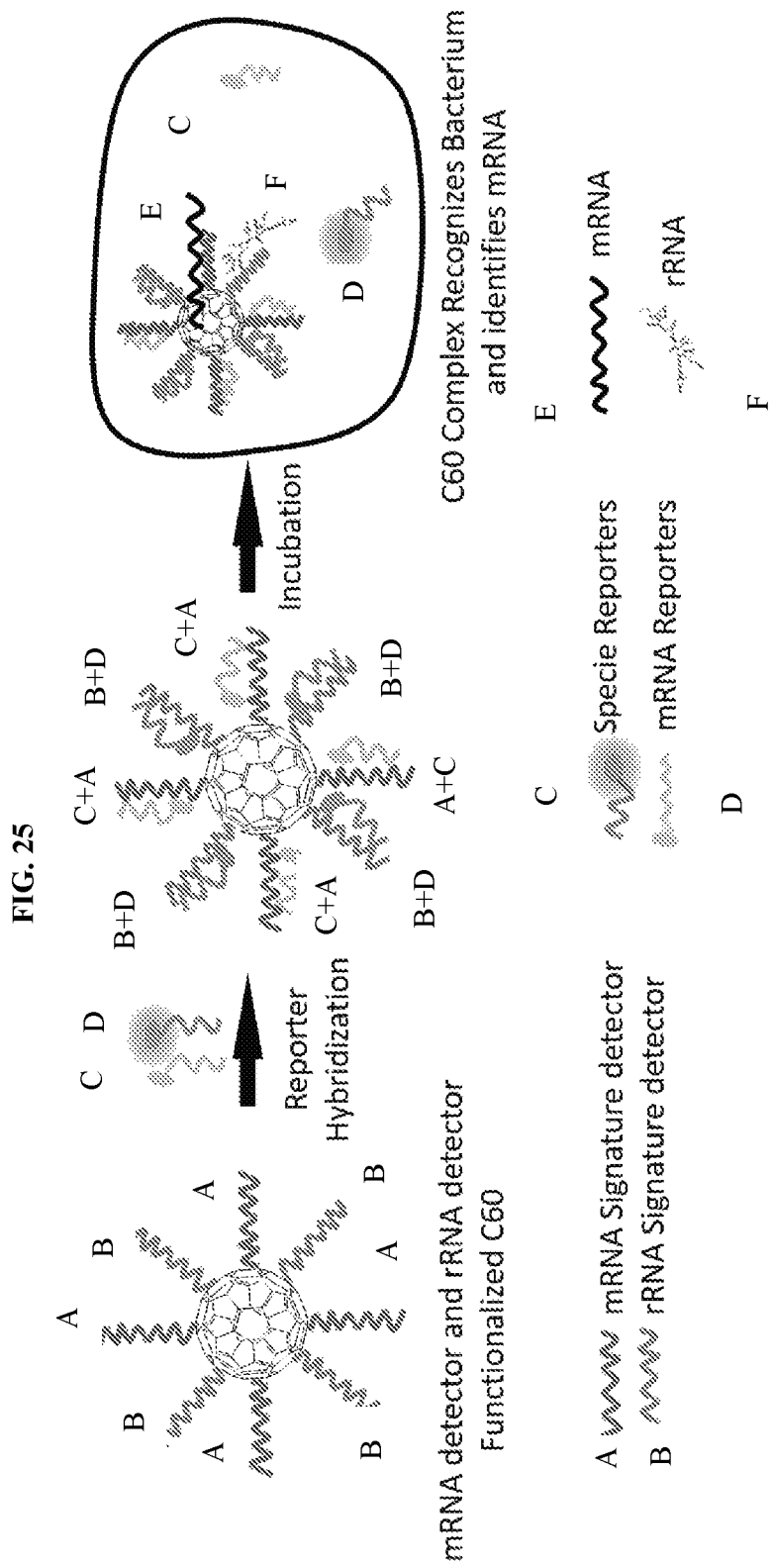
FIG. 25 is a schematic illustrating a method for simultaneously imaging a specific bacterium by identifying both a specific mRNA sequence and a specific rRNA sequence in the specific species of bacterium

Example 8: Simultaneous Imaging of a Specific Microbe and its mRNA mRNA can be targeted by the disclosed C60 complexes which can be transport through the cellular membrane as demonstrated elsewhere herein. mRNA in a specific microbe can be visualized by delivering one set of functionalized Buckyballs, where each Buckyball is functionalized with two different RNA oligonucleotide/protector layer complex, each with a unique fluorophore. The first set recognizes a specific microorganism, by hybridizing to a unique region of 16S rRNA, and emits at one specific wavelength. The second set targets the mRNA and emits at a second specific wavelength. Thus, if both wavelengths are present then mRNA is expressed in a specific microorganism. Alternatively, two sets of Buckyballs can be synthesized, where each target either rRNA or mRNA. An alternative embodiment comprises a variation with only one step, as shown in FIG. 25:

(1) C60 pyrrolidine-tris acid is functionalized with an rRNA signature sequence and an siRNA. The rRNA is selected to recognize a specific bacterium and the siRNA is selected to bind to a specific mRNA to silence certain cellular functions.

(2) A reporter and a protector hybridize the attached rRNA signature and siRNA, preventing degradation. The reporter is quenched while hybridizing with rRNA signature.

(3) C60-siRNA complex are transported across the cellular membrane. Once inside:

(i) The rRNA recognizes the bacterium by hybridizing with a specific rRNA sequence and releases the reporter, thereby illuminating the bacterium.

(ii) The siRNA recognizes the mRNA and shuts down translation by competitively binding.

The method can be used to visualize an organism, such as a bacterium, and regulate gene expression, such as silencing gene expression or activating gene expression, thus altering cell function.

Example 9: Microfluidic System for Rapid Diagnosis of Microbial Presence

Figure 26:
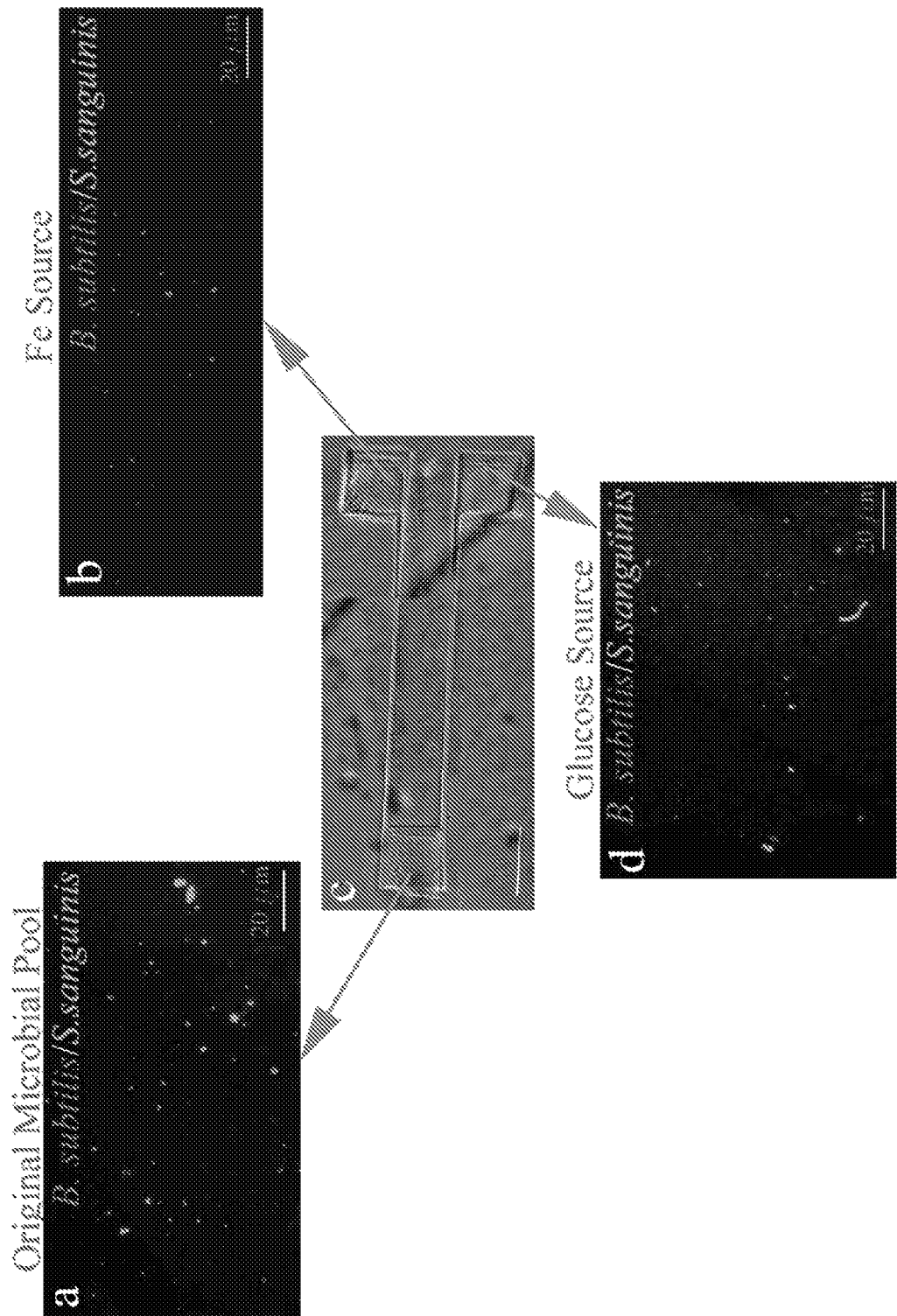
FIG. 26 is an image of a microfluidic system of the invention capable of rapidly diagnosing and differentiating microbial presence. The microfluidic system comprises a source well (left side, panel a) and two sink wells (top right, panel b, and bottom right, panel d) in fluidic communication with each other.

The compositions of the invention can be used in a microfluidic system for the rapid diagnosis of microbial presence as demonstrated in FIG. 26. The system comprises a source well (left hand side) and two sink wells (right hand side, top and bottom). As a proof of concept, a mixture of *B. subtilis* and *S. sanguinis* were prelabeled with the compositions of the invention and deposited in the source well. The sink wells contained iron (FIG. 26, top right well) and glucose (FIG. 26, bottom right well) media, creating a gradient in the channels, helping to draw the microbes to their preferred medium. After 15 minutes, the mixed microorganisms from the source well self selected into their respective sink wells (*B. subtilis* into the iron sink and *S. sanguinis* into the glucose sink) and separation was readily observed due to the fluorescent labeling of the microbes using the compositions of the invention.

In an alternative embodiment of the microfluidic system, a mixture of microbes can similarly be added to the source well without prelabeling using the compositions of the invention. Functionalized Buckyballs corresponding to each microorganism of interest can instead be printed into each sink well, wherein each sink well also contains a medium which would attract the microorganism of interest corresponding to the Buckyball printed into that well. If a microorganism of interest is present in the mixture placed in the source well, it will migrate to the sink well containing its preferred medium, internalize the functionalized Buckyball of the invention containing the matching RNA oligonucleotide and emit a signal. An imaging device can be used to rapidly image the wells of such a system and determine the presence or absence of one or more microbial species as well as the relative abundance of each species.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of selectively labeling a specific species of microorganism in a sample, the method comprising:
    a) functionalizing a Buckminsterfullerene molecule with one or more RNA oligonucleotides complementary to one or more species specific signature RNA sequences of the microorganism in the sample;
    b) hybridizing the one or more RNA oligonucleotides to protecting layers comprising segments of DNA or RNA and a detectable label; and
    c) contacting the sample with the functionalized Buckminsterfullerene molecule for a period of time;
    wherein, the detectable label is not detected when the protecting layers are hybridized to the one or more RNA oligonucleotides and the detectable label is detected when the protecting layers are not hybridized, thereby selectively labeling a specific species of microorganism in the sample.

2. The method of claim 1, wherein the one or more species specific signature RNA sequences are 16S rRNA sequences or mRNA sequences.

3. The method of claim 1, wherein the one or more RNA oligonucleotides are selected by bioinformatics analysis.

4. The method of claim 1, wherein the protecting layers are about 75% complementary to the corresponding RNA oligonucleotides.

5. The method of claim 1, wherein the one or more RNA oligonucleotides are each independently about 80% to a 100% complementary to the corresponding species specific signature RNA sequences.

6. The method of claim 1, wherein the one or more RNA oligonucleotides each independently comprise about 20 to about 50 individual nucleotides.

7. The method of claim 1, wherein two or more specific species of microorganisms are labelled simultaneously with different functionalized Buckminsterfullerene molecules specific for each organism, and wherein each different functionalized Buckminsterfullerene comprises a unique detectable label such that each species of microorganism is labelled with a unique detectable label corresponding to that specific species.

8. The method of claim 7, wherein the presence or absence of the two or more specific species of microorganisms can be determined by detecting the presence or absence of the corresponding unique detectable label.

9. The method of claim 7, wherein the two or more specific species of microorganisms are contained in a single mixed sample.

10. The method of claim 7, wherein the relative abundance of each of the two or more specific species of microorganism is determined by measuring the relative intensity of the two or more unique detectable labels.

11. The method of claim 1, wherein the microorganisms are live microorganisms.

12. The method of claim 1, wherein the microorganism is selected from the group consisting of bacteria, fungi, archaea and protists.

13. The method of claim 1, wherein the microorganism is labeled in a medium selected from the group consisting of a solution, an organic matrix and a soil matrix.

14. The method of claim 13, wherein the functionalized Buckminsterfullerene molecules are functionalized so that they do not adhere or stick to the medium and can be removed from the medium.

15. The method of claim 1, wherein the Buckminsterfullerene molecule is selected from the group consisting of C60 Buckminsterfullerene, C70 Buckminsterfullerene and C60-pyrrolidine tris acid Buckminsterfullerene.

16. The method of claim 1, wherein the detectable label is selected from the group consisting of a fluorescent tag, a radioactive isotope, an amino acid, a nucleic acid, and a peptide.

17. The method of claim 16, wherein the detectable label is selected from the group consisting of glycine, tryptophan, arginine, cysteine, fBSA, $^{14}$C, $^{125}$I and cy3/6-FAM.

18. The method of claim 1, wherein the detectable label is detected using a method selected from the group consisting of autoradiography, fluorescence microscopy, X-ray fluorescence microscopy, UV-vis spectroscopy, TEM and fluorescent spectroscopy.

19. The method of claim 1, wherein the microorganism internalizes the functionalized Buckminsterfullerene.

20. The method of claim 1, wherein identification of the microorganism does not require sample fixation.

21. A method of labeling and identifying a microorganism, the method comprising:
   a) functionalizing a Buckminsterfullerene molecule with a detectable label;
   b) incubating the microorganism with the functionalized Buckminsterfullerene molecule for a period of time.

22. The method of claim 21, wherein the Buckminsterfullerene molecule is selected from the group consisting of C60 Buckminsterfullerene, C70 Buckminsterfullerene and C60-pyrrolidine tris acid Buckminsterfullerene.

23. The method of claim 21, wherein the detectable label is selected from the group consisting of a fluorescent tag, a radioactive isotope, an amino acid, a nucleic acid, and a peptide.

24. The method of claim 23, wherein the detectable label is selected from the group consisting of glycine, tryptophan, arginine, cysteine, fBSA $^{14}$C, $^{125}$I, and cy3/6-FAM.

25. The method of claim 21, wherein the detectable label is detected using a method selected from the group consisting of autoradiography, fluorescence microscopy, X-ray fluorescence microscopy, UV-vis spectroscopy, TEM and fluorescent spectroscopy.

26. The method of claim 21, wherein the microorganism internalizes the functionalized Buckminsterfullerene.

27. The method of claim 21, wherein more than one microorganism is labeled and live microorganisms are differentiated from dead microorganisms.

28. The method of claim 27, wherein dead microorganisms internalize more of the functionalized Buckminsterfullerene molecules than living microorganisms.

29. The method of claim 21, wherein identification of the microorganism does not require sample fixation.

30. The method of claim 21, wherein the microorganism is selected from the group consisting of bacteria, fungi, archaea and protists.

31. A method of detecting gene expression in a living microorganism, the method comprising:
   a) functionalizing a Buckminsterfullerene molecule with one or more RNA oligonucleotides complementary to one or more mRNA segments of interest corresponding to a gene of interest;
   b) hybridizing the one or more RNA oligonucleotides to one or more complementary protecting layers comprising segments of DNA or RNA and a detectable label; and
   c) contacting a sample containing a living microorganism with the functionalized Buckminsterfullerene molecule for a period of time;
   wherein, the detectable label is not detected when the protecting layers are hybridized to the one or more RNA oligonucleotides and the detectable label is detected when the protecting layers are not hybridized, thereby detecting gene expression in a living microorganism.

32. A system for labelling, identifying, and differentiating living microorganisms of different species within a sample, the system comprising:
   a) one or more source wells comprising one or more species of microorganisms; and
   b) one or more sink wells, wherein each sink well comprises a different type of functionalized Buckminsterfullerene molecule, bound to a different detectable label, to identify different species of microorganisms, wherein the Buckminsterfullerene molecules are functionalized with one or more RNA oligonucleotides complementary to one or more species specific signature RNA sequences of the microorganisms in the sample, wherein the one or more RNA oligonucleotides are hybridized to protecting layers comprising segments of DNA or RNA and a detectable label, wherein the detectable label is not detected when the protecting layers are hybridized to the one or more RNA oligonucleotides and the detectable label is detected when the protecting layers are not hybridized to the one or more RNA oligonucleotides;
   wherein the one or more source wells and the one or more sink wells are in fluidic communication with each other to allow the microorganisms to migrate from the one or more source wells to the one or more sink wells and internalize the one or more functionalized Buckminsterfullerene molecules; and
   wherein the microorganisms emit a signal if in contact with a Buckminsterfullerene molecule comprising an RNA oligonucleotide which matches a species specific signature RNA sequence within the microorganism.

33. The system of claim 32, wherein the number of sink wells is equivalent to the number of microorganism species of interest within the sample.

34. The system of claim 32, wherein each sink well further comprises a microbial attractant which attracts the microorganism species of interest matching the functionalized Buckminsterfullerene molecule present in that same sink well.

35. The system of claim 32, wherein the microbial attractant is a nutrient, mineral or environmental condition meant to draw the microorganism of interest to the sink well.

36. The system of claim 35, wherein the microbial attractant is one or more conditions selected from the group consisting of a sugar gradient, a protein gradient, a metal ion gradient, a temperature gradient, a salinity gradient, a light gradient and a specific wavelength of light.

37. The system of claim 32, wherein the functionalized Buckminsterfullerene molecules are printed into the one or more sink wells.

38. The system of claim 32, wherein the one or more species specific signature RNA sequences are 16S rRNA sequences or mRNA sequences.

39. The system of claim 32, wherein the one or more RNA oligonucleotides are selected by bioinformatics analysis.

40. The system of claim 32, wherein the protecting layers are about 75% complementary to the corresponding RNA oligonucleotides.

41. The system of claim 32, wherein the one or more RNA oligonucleotides are each independently about 80% to a 100% complementary to the corresponding species specific signature RNA sequences.

42. The system of claim 32, wherein the one or more RNA oligonucleotides each independently comprise about 20 to about 50 individual nucleotides.

43. The system of claim 32, wherein the microorganisms are selected from the group consisting of bacteria, fungi, archaea and protists.

44. The system of claim 32, wherein the Buckminsterfullerene molecules are selected from the group consisting of C60 Buckminsterfullerene, C70 Buckminsterfullerene and C60-pyrrolidine tris acid Buckminsterfullerene.

45. The system of claim 32, wherein the detectable labels are selected from the group consisting of fluorescent tags, radioactive isotopes, amino acids, nucleic acids, and peptides.

46. A functionalized Buckminsterfullerene composition comprising:
   C60-pyrrolidine tris acid Buckminsterfullerene;
   one or more non-coding RNA oligonucleotides; and one or more detectable labels selected from the group consisting of a fluorescent tag, a radioactive isotope, an amino acid, a nucleic acid, and a peptide.

47. The functionalized Buckminsterfullerene composition of claim 46, wherein the one or more RNA oligonucleotides each independently comprise about 20 to about 50 individual nucleotides.

48. The functionalized Buckminsterfullerene composition of claim 46, further comprising protecting layers, wherein the protecting layers are segments of DNA or RNA which can be hybridized to the one or more RNA oligonucleotides.

49. The functionalized Buckminsterfullerene composition of claim 48, wherein the protecting layers are about 75% complementary to the corresponding RNA oligonucleotides.

50. The functionalized Buckminsterfullerene composition of claim 46, wherein the one or more detectable labels are bound to the protecting layers.

* * * * *